US007361329B2

(12) United States Patent
Schall et al.

(10) Patent No.: US 7,361,329 B2
(45) Date of Patent: *Apr. 22, 2008

(54) COMPOSITIONS FOR INDUCING AN IMMUNE RESPONSE

(75) Inventors: Thomas J. Schall, Palo Alto, CA (US); Maureen Howard, Los Altos, CA (US); Robert Berkovitz, San Francisco, CA (US); Brett Premack, San Francisco, CA (US); Dale Talbot, San Francisco, CA (US)

(73) Assignee: ChemoCentryx, Inc., Mountain View, CA (US)

( * ) Notice: Subject to any disclaimer, the term of this patent is extended or adjusted under 35 U.S.C. 154(b) by 1181 days.

This patent is subject to a terminal disclaimer.

(21) Appl. No.: 10/001,221

(22) Filed: Oct. 30, 2001

(65) Prior Publication Data

US 2003/0108515 A1   Jun. 12, 2003

Related U.S. Application Data

(63) Continuation-in-part of application No. 09/834,814, filed on Apr. 12, 2001, now abandoned, application No. 10/001,221, which is a continuation-in-part of application No. PCT/US01/12162, filed on Apr. 12, 2001.

(60) Provisional application No. 60/198,839, filed on Apr. 21, 2000.

(51) Int. Cl.
*A61K 45/00* (2006.01)
*C07K 14/005* (2006.01)

(52) U.S. Cl. ..................... 424/85.1; 530/351
(58) Field of Classification Search .............. 424/85.1, 424/278.1; 514/21
See application file for complete search history.

(56) References Cited

U.S. PATENT DOCUMENTS

| 5,141,867 | A | 8/1992 | Ivanoff et al. |
| 5,284,753 | A | 2/1994 | Goodwin, Jr. |
| 5,705,151 | A | 1/1998 | Dow et al. |
| 5,837,247 | A | 11/1998 | Oppenhelm et al. |
| 5,935,568 | A | 8/1999 | Dow et al. |
| 5,994,126 | A | 11/1999 | Steinman et al. |

FOREIGN PATENT DOCUMENTS

| EP | 0 974 357 A | 1/2000 |
| WO | WO 94/28916 A1 | 12/1994 |
| WO | WO 96/11279 A2 | 4/1996 |
| WO | WO 96/36366 A1 | 11/1996 |
| WO | WO 97/19696 A1 | 6/1997 |
| WO | WO 98 04282 A | 2/1998 |
| WO | WO 98/15285 A1 | 4/1998 |
| WO | WO 98/33520 * | 8/1998 |
| WO | WO 99 29728 A | 6/1999 |
| WO | WO 99/43839 A1 | 9/1999 |
| WO | WO 99/53960 A2 | 10/1999 |
| WO | WO 00/22124 A2 | 4/2000 |
| WO | WO 01/80882 A3 | 11/2001 |
| WO | WO 01 80887 A | 11/2001 |

OTHER PUBLICATIONS

Mohamadzadeh et al (Archives of Dermatological Research, 1997, vol. 289, pp. 435-439).*
Orlofsky et al (Cytokine, Mar. 2000, vol. 12, pp. 220-228).*
Kedar et al (Advances in Cancer Research, 1992, vol. 59, pp. 245-322).*
Saederup et al (PNAS, Sep. 1999, vol. 96, pp. 10881-10886).*
Wells, James "Additivity of Mutational Effects in Proteins" *Biochemistry*, Sep. 18, 1990; p. 8509-8517, vol. 29, No. 37.
Wu, George Y., et al.; Receptor-mediated in Vitro Gene Transformation by a Soluble DNA Carrier System; *The Journal of Biological Chemistry*; 1987; pp. 4429-4432; vol. 262, No. 10.
Xiang, Zhiquan, et al.; Manipulation of the Immune Response to a Plasmid-Encoded Viral Antigen by Coinoculation with Plasmids Expressing Cytokines; *Immunity*; Feb. 1995; pp. 129-135; vol. 2.
Baggiolini et al., "Chemokines and leukocyte traffic", *Nature*, vol. 392, 1998, pp. 565-568.
Baures, "Design, Synthesis, and Dopamine Receptor Modulating Activity of Diketopiperazine Peptidomimetics of L-Prolyl-L-leucylglycinamide", *J. Med. Chem.*, vol. 40, 1997, pp. 3594-3600.
Beaulieu, "Potent HIV Protease Inhibitors Containing a Novel (Hydroxyethyl)amide isostere" *J. Med. Chem.*, vol. 40, 1997, pp. 2164-2176.
Bluel et al., "A highly efficacious lymphocyte chemoattractant, stromal cell-derived factor 1 (SDF-1)", *J. Exp. Med.*, vol. 184, No. 3, 1996, pp. 1101-1109.
Bozarth et al., "An improved method for the quantitation of cellular migration: Role of alpha-v-beta-3 integrin in endothelial and smooth muscle cell migration", *Meth. Cell Science*, vol. 19, 1997, pp. 179-187.
Brady, S.F. et al. "Discovery and Development of the Novel Potent Orally Active Thrombin Inhibitor N-(9-Hydroxy-9 fluorenecarboxy)prolyl trans-4-Aminocyclohexylmethyl amide (L-372,460): Coapplication of structure-based design and rapid multiple analogue synthesis on solid support", *J. Med. Chem.*, vol. 41, 1998, pp. 401-406.

(Continued)

*Primary Examiner*—Karen A. Canella
(74) *Attorney, Agent, or Firm*—Townsend and Townsend and Crew LLP

(57) ABSTRACT

This application relates generally to enhancing immune responses. Such immune responses may be elicited by vaccine administration. Compositions and methods for inducing or enhancing an immune response to an antigen are provided. The compositions and methods are useful for, among other things, vaccine formulation for therapeutic and prophylactic vaccination (immunization) and for production of useful antibodies (e.g., monoclonal antibodies for therapeutic or diagnostic use).

36 Claims, 2 Drawing Sheets

OTHER PUBLICATIONS

Campbell, J. et al., "6-C-kine (SLC), a Lymphocyte adhesion-triggering chemokine expressed by high endothelium, is an agonist for the MIP-3beta receptor CCR7", *J. Cell Biol.*, vol. 141, 1998, pp. 1053.

Cella, M. et al., "Maturation, activation, and protection of dentritic cells induced by double-stranded RNA", *J. Exp. Med.*, vol. 189, 1999, pp. 821-829.

Chan, V. et al., "Secondary lymphoid-tissue chemokine (SLC) is chemotactic for mature dendritic cells", *Blood*, vol. 93, 1999, pp. 3610.

Davatelis et al., "Cloning and characterization of a cDNA for murine macrophage inflammatory protein (MIP), a novel monkine with inflammatory and chemokinetic properties", *J. Exp. Med.*, vol. 167, No. 6, 1988, pp. 1939-1944.

Dieu, M. et al., "Selective recruitment of immature and mature dendritic cells by distinct chemokines expressed in different anatomic sites", *J. Exp. Med.*, vol. 188, 1998, pp. 373.

Farber et al., "A macrophage mRNA selectively induced by gamma-interferon encodes a member of the platelt factor 4 family of cytokines", *Proc. Natl. Acad. Sci. USA*, vol. 87, No. 14, 1990, pp. 5238-5242.

Forssmann et al., "CKbeta8, a novel CC chemokine that predominantly acts on monocytes", *FEBS Lett.*, vol. 408, No. 2, 1997, pp. 211-216.

Gunn et al., "A B-cell-homing chemokine made in lymphoid follicles activates Burkitt's lymphoma receptor-1", *Nature*, vol. 391, No. 6669, 1998, pp. 799-803.

Hedrick et al., "Identification and characterization of a novel beta chemokine containing six conserved cysteines", *J. Immunol.*, vol. 159, No. 4, 1997, pp. 1589-1593.

Hieshima et al., "Molecular cloning of a novel human CC chemokine liver and activation-regulated chemokine (LARC) expressed in liver. Chemotactic activity for lymphocytes and gene localization on chromosome 2", *J. Biol. Chem.*, vol. 272, No. 9, 1997, pp. 5846-5853.

Irving et al., "Two inflammatory mediator cytokine genes are closely linked and variably amplified on chromosome 17q", *Nuc. Acid Res.*, vol. 18, 1990, pp. 3261-3270.

Keller, H., "Chemotaxis and its significance for leucocyte accumulation", *Agents Actions*, vol. 2, 1972, pp. 161-169.

Kellerman S. et al., "The CC chemokine receptor-7 ligands 6Ckine and macrophage inflammatory protein-3beta are potent chemoattractants for in vitro- and in vivo-derived dendritic cells", *J. Immunol*, vol. 162, 1999, pp. 3859.

Lipes et al., "Identification, cloning, and characterization of an immune activation gene", *Proc. Natl. Acad. Sci. USA*, vol. 85, 1998, pp. 9704.

MacDonald et al., "Spliced mRNA encoding the murine cytomegalovirus chemokine homolog predicts a beta chemokine of novel structure", *J. Virol.*, vol. 73, No. 5, 1999, pp. 3682-3691.

Macphee et al., "Identification of a truncated form of the CC chemokine CK beta-8 demonstrating greatly enhanced biological activity", *J Immunol.*, vol. 161 No. 11, 1998, pp. 6273-6279.

Misicka, A. et al., "Synthesis and biological properties of beta-MePhe$^3$ analogues of deltorphin I and dermenkephalin: influence of biased $_x{}^1$ of the Phe$^3$ residues on peptide recognition for δ-opioid receptors", *J. Pept. Res.*, vol. 50, 1997, pp. 48-54.

Nagasawa et al., "Molecular cloning and structure of a pre-B-cell growth-stimulating factor", *Proc. Natl. Acad. Sci. USA*, vol. 91, No. 6, 1994, pp. 2305-2309.

Nicholas et al., "Kaposi's sarcoma-associated human herpesvirus-8 encodes homologues of macrophage inflammatory protein-1 and interleukin-6", *Nat. Med.*, vol. 3, No. 3, 1997, pp. 287-292.

Obaru et al., "A cDNA clone used to study mRNA inducible in human tonsillar lymphocytes by a tumor promoter", *J. Biochem.*, vol. 99, No. 3, 1986, pp. 885-894.

Orlofsky et al., "Novel expression pattern of a new member of the MIP family of cytokine-like genes", *Cell Regulation*, vol. 2, 1991, pp. 403-412.

Poltorak et al., "MIP-1 gamma: a molecular cloning, expression, and biological activities of a novel CC chemokine that is constitutively secreted in vivo", *Inflamm*, vol. 45, No. 3, 1995, pp. 207-219.

Proudfoot, et al., "Extension of recombinant human RANTES by the retention of the initiating methionine produces a potent antagonist", *J. Biol. Chem.*, vol. 271, No. 5, 1996, pp. 2599-2603.

Rothenberg et al., "Murine eotaxin: an eosinophil chemoattractant inducible in endothelial cells and in interlukin 4-induced tumor suppression", *Proc. Natl. Acad. Sci. USA*, vol. 92, No. 19, 1995, pp. 8960-8964.

Saederup et al., "Cytomegalovirus-encoded beta chemokine promotes monocyte-associated viremia in the host", *Proc. Natl. Acad. Sci. USA*, vol. 96, No. 19, 1999, pp. 10881-10886.

Sarafi et al., Murine monocyte chemoattractant protein (MCP)-5: a novel CC chemokine that is a structural and functional homologue of human MCP-1, *J. Exp. Med.*, vol. 185, No. 1, 1997, pp. 99-109.

Schall et al., "A human T cell-specific molecule is a member of a new gene family", *J. Immunol.*, vol. 141, 1988, pp. 1018.

Schall et al., "Molecular cloning and expression of the murine RANTES cytokine: structural and functional conservation between mouse and man", *Eur. J. Immunol.*, vol. 22, No. 6, 1992, pp. 1477-1481.

Schaniel et al., "Activated Murine B Lymphocytes and Dendritic Cells Produce a Novel CC Chemokine which Acts Selectively on Activated T Cells", *J. Exp. Med.*, vol. 188, No. 3, 1998, pp. 451-463.

Schulz-Kappe et al., "HCC-1, a novel chemokine from human plasma", *J. Exp. Med.*, vol. 183, No. 1, 1996, pp. 295-299.

Sherry et al., "Resolution of the two components of macrophage inflammatory protein 1, and cloning and characterization of on of those components, macrophage inflammatory protein 1 beta", *J. Exp. Med.*, vol. 168, No. 6, 1988, pp. 2251-2259.

Tashiro et al., "Signal sequence trap: a cloning strategy for secreted proteins and type I membrane proteins", *Science*, vol. 261, No. 5121, 1993, pp. 600-603.

Tekamp-Olson et al., "Cloning and characterization of cDNAs for murine macrophage inflammatory protein 2 and its human homologues", *J. Exp. Med.*, vol. 172, No. 3, 1990, pp. 911-919.

Thirion et al., "Mouse macrophage derived monocyte chemotactic protein-3: cDNA cloning and identification as MARC/FIC", *Biochem. Biophys. Res. Commun.*, vol. 201, No. 2, 1994, pp. 493-499.

Ugoccioni et al., "Monocyte chemotactic protein 4 (MCP-4), a novel structural and functional analogue of MCP-3 and eotaxin", *J. Exp. Med.*, vol. 183, 1996, pp. 2379.

Van Damme et al., "Production and identification of natural monocyte chemotactic protein from virally infected murine fibroblasts. Relationship with the product of the mouse competence (JE) gene", *Eur. J. Biochem.*, vol. 199, No. 1, 1999, pp. 223-229.

Van Damme et al., "Structural and functional identification of two humans, tumor-derived monocyte chemotactic proteins (MCP-2 and MCP-3) belonging to the chemokine family", *J. Exp. Med.*, vol. 176., No. 1, 1992, pp. 59-65.

Verdijk, R. et al., "Polyriboinosinic polyribocytidylic Acid (Poly(I:C)) induces stable maturation of functionally active human dendritic cells", *J. Immunol.*, vol. 1, 1999, pp. 57-61.

Vicari et al., "TECK: a novel CC chemokine specifically expressed by thymic dendritic cells and potentially involved in T cell development", *Immunity*, vol. 7, No. 2, 1997, pp. 291-301.

Wang et al., "Molecular cloning and functional characterization of human MIP-1 delta, a new C-C chemokine related to mouse CCF-18 and C10", *J. Clin. Immunol.*, vol. 18, No. 3, 1998, pp. 214.

Ward S. et al., "Chemokines and T lymphocytes: more than an attraction", *Immunity*, vol. 9, 1998, pp. 1-11.

Yoshida et al., "Molecular cloning of a novel human CC chemokine EBI1-ligand chemokine that is specific functional ligand for EBI1, CCR7", *J. Biol. Chem.*, vol. 272, No. 21, 1997, pp. 13803-13809.

Youn et al., "Characterization of CKbeta8 and CKbeta8-1: two alternatively spliced forms of human beta-chemokine, chemattractants for neutrophils, monocytes, and lymphocytes, and potent agonists at CC chemokine receptor 1", *Blood*, vol. 91, No. 9, 1998, pp. 3118-3126.

Youn et al., "Molecular cloning of leukotactin-1: a novel human beta-chemokine, a chemoattractant for neutrophils, monocytes, and lymphocytes, and a potent agonist at CC chemokine receptors 1 and 3", *J. Immumol.*, vol. 159, No. 11, 1997, pp. 5201-5205.

Zhang, Y, et al., "Synthesis, biological activity, and conformational analysis of peptidomimetic analogues of the *Saccharomyces cerevisiae* alpha-factor tridecapeptide", *Biochemistry*, vol. 37, 1998, pp. 12465-12476.

De Giovanni, Carla et al., "The Prospects For Cancer Gene Therapy", *International Journal of Immunopharmacology*, vol. 22, No. 12, 2000, pp. 1025-1032.

Greaves, David R. et al., "Chemokines and Myeloid Cell Recruitment", *Microbes and Infection*, vol. 2, No. 3, 2000, pp. 331-336.

Banchereau, Jacques and Ralph M. Steinman; Dendritic cells and the control of immunity; Nature; Mar. 19, 1998; pp. 245-252; vol. 392.

Caux, Christophe, et al.; Developmental Pathways of Human Myeloid Dendritic Cells; Dendritic Cells: Biology and Clinical Applications; 1999; pp. 63-92 (chapter 5); Academic Press.

ChemoTx Disposable; Neuro Probe website; Products (1 page) and Protocols (2 pages); Wednesday, Apr. 19, 2000; http://www.neuroprobe.

Chow, Yen-Hung, et al.; Development of Th1 and Th2 Populations and the Nature of Immune Responses to Hepatitis B Virus DNA Vaccines Can Be Modulated by Codelivery of Various Cytokine Genes; *The Journal of Immunology*; 1998; pp. 1320-1329; vol. 160.

Dilloo, Dagmar, et al.; Combined chemokine and cytokine gene transfer enhances antitumor immunity; *Nature Medicine*; Oct. 1996; pp. 1090-1095; vol. 2, No. 10.

Eng, Vicki M., et al.; The Stimulatory Effects of Interleukin (IL)-12 On Hematopoiesis Are Antagonized by IL-12-induced Interferon γ In Vivo; *J. Exp. Med.*; May 1995; pp. 1893-1898; vol. 181.

Eo, Seong Kug, et al.; Modulation of Immunity against Herpes Simplex Virus Infection via Mucosal Genetic Transfer of Plasmid DNA Encoding Chemokines; Journal of Virology; Jan. 2001; pp. 569-578; vol. 75, No. 2.

GenBank Accession No. P27784, Aug. 1, 1992.

Khudyakov, Yu E.; et al. Linear B-Cell Epitopes of the NS3-NS4-NS5 Proteins of the Hepatitis C. Virus as Modeled with Synthetic Peptides; *Virology*; 1995; pp. 666-672; vol. 206.

Liljeqvist, Sissela & Stahl, "Production of recombinant subunit vaccines: protein immunogens, live delivery systems and nucleic acid vaccines" Journal of Biotechnology, 1999, pp. 1-33, vol. 73, Elsevier.

Moldoveanu, Zina, et al.; Immune responses induced by administration of encapsidated poliovirus replicons which express HIV-1 gag and envelope proteins; *Vaccine*; 1995; pp. 1013-1022: vol. 13, No. 11.

Orange, Jordan S.; et al.; Mechanism of Interleukin 12-mediated Toxicities during Experimental Viral Infections: Role of Tumor Necrosis Factor and Glucocorticoids; *J. Exp. Med.*; Mar. 1995; pp. 901-914; vol. 181.

R & D Systems 2000 Catalog; front and back cover, Contents in Brief, Ordering Information, (p. i) Contact Information (p. ii), Cytokines & Related Molecules (p. 93-94 and 162), Antibodies (p. 163-164 and 291), 2000.

Ramshaw, Ian; et al.; Expression of Cytokines by Recombinant Vaccinia Viruses: A Model for Studying Cytokines in Virus Infections in vivo; *Immunological Reviews*; 1992; pp. 157-182; No. 127.

Tsuji, T., et al.; HIV-1-specific cell-mediated immunity is enhanced by co-inoculation of TCA3 expression plasmid with DNA vaccine; *Immunology*; 1997; pp. 1-6; vol. 90.

\* cited by examiner

| | | |
|---|---|---|
| hMCP-2 | QPDSVSIPIT C C FNVINRKIPIQRLESYTRITNIQ C PKEAVIFKTQRGKEV C ADPKERWVRDSMKHLDQIFQNLKP | |
| mC10 | GLIQEMEKEDRRYNPPIIHQGFQDTSSD C C FSYATQ IPCKRFI YYFPTSGG C IKPGIIFISRRGTQV C ADPSDRRVQRCLSTLKQGPRSGNKVIA | |
| mMDC | GPYGANVEDSI C C QDYIRHPLPS RLVKEFFWTSKS C RKPGVVLITVKNRDI C ADPRQVWKKLLHKLS | |
| | | |
| mC10/hMCP2 | GLIQEMEKEDRRYNPPIIHQGFQDTSSD C C FNVINRKIPIQRLESYTRITNIQ C PKEAVIFKTQRGKEV C ADPKERWVRDSMKHLDQIFQNLKP | |
| hMCP2/mC10 | QPDSVSIPIT C C FSYATQ IPCKRFI YYFPTSGG C IKPGIIFISRRGTQV C ADPSDRRVQRCLSTLKQGPRSGNKVIA | |
| | | |
| mMDC/hMCP2 | GPYGANVEDSI C C FNVINRKIPIQRLESYTRITNIQ C PKEAVIFKTQRGKEV C ADPKERWVRDSMKHLDQIFQNLKP | |
| hMCP2/mMDC | QPDSVSIPIT C C QDYIRHPLPS RLVKEFFWTSKS C RKPGVVLITVKNRDI C ADPRQVWKKLLHKLS | |

FIG. 2.

SEQUENCE LISTING

<160> NUMBER OF SEQ ID NOS: 7

<210> SEQ ID NO 1
<211> LENGTH: 76
<212> TYPE: PRT
<213> ORGANISM: Homo sapiens

<400> SEQUENCE: 1

Gln Pro Asp Ser Val Ser Ile Pro Ile Thr Cys Cys Phe Asn Val Ile
1               5                   10                  15

Asn Arg Lys Ile Pro Ile Gln Arg Leu Glu Ser Tyr Thr Arg Ile Thr
            20                  25                  30

Asn Ile Gln Cys Pro Lys Glu Ala Val Ile Phe Lys Thr Gln Arg Gly
        35                  40                  45

Lys Glu Val Cys Ala Asp Pro Lys Glu Arg Trp Val Arg Asp Ser Met
    50                  55                  60

Lys His Leu Asp Gln Ile Phe Gln Asn Leu Lys Pro
65                  70                  75

<210> SEQ ID NO 2
<211> LENGTH: 95
<212> TYPE: PRT
<213> ORGANISM: Homo sapiens

<400> SEQUENCE: 2

Gly Leu Ile Gln Glu Met Glu Lys Glu Asp Arg Arg Tyr Asn Pro Pro
1               5                   10                  15

Ile Ile His Gln Gly Phe Gln Asp Thr Ser Ser Asp Cys Cys Phe Ser
            20                  25                  30

Tyr Ala Thr Gln Ile Pro Cys Lys Arg Phe Ile Tyr Tyr Phe Pro Thr
        35                  40                  45

Ser Gly Gly Cys Ile Lys Pro Gly Ile Ile Phe Ile Ser Arg Arg Gly
    50                  55                  60

```
Thr Gln Val Cys Ala Asp Pro Ser Asp Arg Arg Val Gln Arg Cys Leu
 65                  70                  75                  80

Ser Thr Leu Lys Gln Gly Pro Arg Ser Gly Asn Lys Val Ile Ala
                 85                  90                  95

<210> SEQ ID NO 3
<211> LENGTH: 68
<212> TYPE: PRT
<213> ORGANISM: Homo sapiens

<400> SEQUENCE: 3

Gly Pro Tyr Gly Ala Asn Val Glu Asp Ser Ile Cys Cys Gln Asp Tyr
  1               5                  10                  15

Ile Arg His Pro Leu Pro Ser Arg Leu Val Lys Glu Phe Phe Trp Thr
                 20                  25                  30

Ser Lys Ser Cys Arg Lys Pro Gly Val Val Leu Ile Thr Val Lys Asn
             35                  40                  45

Arg Asp Ile Cys Ala Asp Pro Arg Gln Val Trp Val Lys Leu Leu
         50                  55                  60

His Lys Leu Ser
 65

<210> SEQ ID NO 4
<211> LENGTH: 94
<212> TYPE: PRT
<213> ORGANISM: Artificial sequence
<220> FEATURE:
<223> OTHER INFORMATION: Chimeric molecule

<400> SEQUENCE: 4

Gly Leu Ile Gln Glu Met Glu Lys Glu Asp Arg Arg Tyr Asn Pro Pro
  1               5                  10                  15

Ile Ile His Gln Gly Phe Gln Asp Thr Ser Ser Asp Cys Cys Phe Asn
                 20                  25                  30

Val Ile Asn Arg Lys Ile Pro Ile Gln Arg Leu Glu Ser Tyr Thr Arg
             35                  40                  45

Ile Thr Asn Ile Gln Cys Pro Lys Glu Ala Val Ile Phe Lys Thr Gln
         50                  55                  60

Arg Gly Lys Glu Val Cys Ala Asp Pro Lys Glu Arg Trp Val Arg Asp
 65                  70                  75                  80

Ser Met Lys His Leu Asp Gln Ile Phe Gln Asn Leu Lys Pro
                 85                  90

<210> SEQ ID NO 5
<211> LENGTH: 77
<212> TYPE: PRT
<213> ORGANISM: Artificial sequence
<220> FEATURE:
<223> OTHER INFORMATION: Chimeric molecule

<400> SEQUENCE: 5

Gln Pro Asp Ser Val Ser Ile Pro Ile Thr Cys Cys Phe Ser Tyr Ala
  1               5                  10                  15

Thr Gln Ile Pro Cys Lys Arg Phe Ile Tyr Tyr Phe Pro Thr Ser Gly
                 20                  25                  30

Gly Cys Ile Lys Pro Gly Ile Ile Phe Ile Ser Arg Arg Gly Thr Gln
             35                  40                  45

Val Cys Ala Asp Pro Ser Asp Arg Arg Val Gln Arg Cys Leu Ser Thr
         50                  55                  60
```

-continued

```
Leu Lys Gln Gly Pro Arg Ser Gly Asn Lys Val Ile Ala
65                  70                  75

<210> SEQ ID NO 6
<211> LENGTH: 78
<212> TYPE: PRT
<213> ORGANISM: Artificial sequence
<220> FEATURE:
<223> OTHER INFORMATION: Chimeric molecule

<400> SEQUENCE: 6

Gly Pro Tyr Gly Ala Asn Val Glu Asp Ser Ile Cys Cys Phe Asn Val
1               5                   10                  15

Ile Asn Arg Lys Ile Pro Ile Gln Arg Leu Glu Ser Tyr Thr Arg Ile
            20                  25                  30

Thr Asn Ile Gln Cys Pro Lys Glu Ala Val Ile Phe Lys Lys Thr Gln
        35                  40                  45

Arg Gly Lys Glu Val Cys Ala Asp Pro Lys Glu Arg Trp Val Arg Asp
    50                  55                  60

Ser Met Lys His Leu Asp Gln Ile Phe Gln Asn Leu Lys Pro
65                  70                  75

<210> SEQ ID NO 7
<211> LENGTH: 67
<212> TYPE: PRT
<213> ORGANISM: Artificial sequence
<220> FEATURE:
<223> OTHER INFORMATION: Chimeric molecule

<400> SEQUENCE: 7

Gln Pro Asp Ser Val Ser Ile Pro Ile Thr Cys Cys Gln Asp Tyr Ile
1               5                   10                  15

Arg His Pro Leu Pro Ser Arg Leu Val Lys Glu Phe Phe Trp Thr Ser
            20                  25                  30

Lys Ser Cys Arg Lys Pro Gly Val Val Leu Ile Thr Val Lys Asn Arg
        35                  40                  45

Asp Ile Cys Ala Asp Pro Arg Gln Val Trp Val Lys Lys Leu Leu His
    50                  55                  60

Lys Leu Ser
65
```

COMPOSITIONS FOR INDUCING AN IMMUNE RESPONSE

RELATED APPLICATIONS

This application is a continuation-in-part of U.S. application Ser. No. 09/834,814, filed Apr. 12, 2001, now abandoned which is incorporated by reference in its entirety, and a continuation-in-part of PCT Application PCT/US01/12162, filed Apr. 12, 2001, both of which claim the benefit of U.S. Provisional Application No. 60/198,839, filed Apr. 21, 2000.

FIELD OF THE INVENTION

This application relates generally to enhancing immune responses. Such immune responses may be elicited by vaccine administration. Compositions and methods for inducing or enhancing an immune response to an antigen are provided. The compositions and methods are useful for, among other things, vaccine formulation for therapeutic and prophylactic vaccination (immunization) and for production of useful antibodies (e.g., monoclonal antibodies for therapeutic or diagnostic use).

BACKGROUND

Immunization, or vaccination, is a widely used method to elicit an immune response to an antigen for prophylactic purposes. For example, by administering a harmless form of an antigen from a pathogen, such as an attenuated virus, the production of antibodies and stimulation of immune cells specific for the harmful form of the pathogen occurs. However, present immunization methods are not effective for all antigens. Moreover, there is a considerable lag time from immunization until the immune system provides protection for the subject. Improved methods and reagents for vaccination are desired by the medical community.

SUMMARY

The invention relates to new vaccines and immunization methods.

In one aspect, the invention is a method for eliciting an immune response to an antigen in a subject comprising administering at least one antigen-presenting cell (APC) chemotaxin and an antigen is presented. APC chemotaxins are chemotactic for immature and/or mature dendritic cells. In some aspects, APC chemotaxins are chemotractic specifically for only immature and/or mature dendritic cells.

In another aspect, the invention is a method of enhancing an immune response of a subject to an antigen comprising administering an APC chemotaxin and the antigen. The immune response may comprise an antibody-mediated response; such enhancement comprises an increase in antigen-specific antibodies by at least 2-fold. The immune response may comprise a cell-mediated response.

In another aspect, the invention comprises co-administering the APC chemotaxin and antigen; alternatively, the APC chemotaxin and antigen are administered separately to elicit or enhance an immune response to the antigen.

In another aspect, the invention comprises administering at least two AOC chemotaxins. Such chemotaxins may be a chemokine polypeptide or variant, or a chimera of various chemokines/chemokine domains. Exemplary chemokines include hMIP1α, hMIP1α (70aa), mMIP-1α, hRANTES, hMET-RANTES, mRANTES, hHCC-1, hMPIF-1, hMPIF-1 (22-137), hMPIF-1 (46-137), hMIP-1δ, hMCP-4, mMCP-5, mMARC, mEotaxin, mMCP-1 (JE), mTECK, mMIP-2, mBLC, hLeukotactin, mMIG, mMIP-1β. hMCP-2, hMCP-3, vMIP-1, hMIP-3α, hMIP-3β, mC10, mMDC, hMIP-1β, vMCK-2, mMIP-1γ, mC10, mMIP-1γ and vMCK-2.

In another aspect, administering APC chemotaxins includes formulating APC chemotaxins in a sustained release pharmaceutical composition.

In another aspect of the invention, antigens are pathogen polypeptides, such as those from *Hepatitis* or *Influenza*, or a tumor adjuvant.

In another aspect of the invention, APC chemotaxins may be administered with adjuvants, such as alum, incomplete Freund's adjuvant, a bacterial capsular polysaccharide, dextran, IL-12, GM-CSF, CD40 ligand, IFN-gamma, IL-1, IL-2, IL-3, IL-4, IL-10, IL-13, IL-18, and a cytokine. In another aspect, the invention comprises multi-valent carriers that may be linked to an APC chemotaxin, antigen and/or adjuvant. Multivalent carriers may be, for example, bacterial capsular polysaccharides (such as *Pneumococci, Streptococci,* or *Meningococci*), a dextran and a genetically engineered vector.

In another aspect, the invention comprises administering with an APC chemotaxin a pharmaceutical carrier.

In another aspect, the invention is administering APC chemotaxins into a solid tumor or the tissue surrounding a solid tumor.

In another aspect, the invention is, the administering of an APC chemotaxin is accomplished by administering a polynucleotide encoding the APC chemotaxin. In another aspect, a polynucleotide encoding an antigen is administered. In other aspect, polynucleotides encoding at least one APC chemotaxin and at least one antigen are administered In another aspect, the invention is a composition comprising at least one APC chemotaxin, and at least one antigen. In a another aspect, the APC chemotaxin is chemotactic for mature or immature dendritic cells; the APC chemotaxin may be specifically chemotactic for mature or immature dendritic cells; that is, the APC chemotaxin is not chemotactic for neutrophil, T cell, B cell, monocyte and/or eosinophil.

In another aspect, the invention is a composition comprising at least two APC chemotaxins. In another aspect, the invention is a composition comprising an APC chemotaxin that is is a chemokine polypeptide or a variant thereof In another aspect, the invention is a composition comprising an APC chemotaxin formulated in a sustained release formulation. In another aspect, the compositions of the invention further comprise at least one pharmaceutically acceptable carrier, such as an adjuvant.

In other aspects, the adjuvant in the compositions of the invention is water, an oil, a saline solution, aqueous dextrose and/or glycerol solution.

In another aspect, the invention is an immunogenic composition comprising a cell exogenously expressing an APC chemotaxin. In a further aspect, APC chemotaxin expressing cells are allogeneic or autologous.

In another aspect, the invention is an immunogenic composition at least one APC chemotaxin and a tumor-associated antigen. Such an antigen may be from an allogeneic or autologous cell.

In another aspect, the invention is an immunogenic composition comprising at least one tumor cell, and at least one cell exogenously expressing an APC chemotaxin. A suitable tumor cell may be a primary tumor cell, such as from an autologous cell or a glioma, glioblastoma, gliosarcoma, astrocytoma, melanoma, breast cancer cell or an ovarian cancer cell. In another aspect, the invention comprises a tumor cell that is quiescent. In other aspects, the various cells of the invention comprise are allogeneic.

In another aspect, the invention is a method of formulating a composition capable of eliciting an immune response to an antigen in a subject comprising isolating a polypeptide having an activity of an APC chemotaxin, and combining the polypeptide with the antigen.

In a further aspect, the invention is a kit comprising a pharmaceutical composition comprising an APC chemotaxin and a pharmaceutically acceptable carrier, and a syringe.

BRIEF DESCRIPTION OF THE DRAWINGS

FIG. 2 shows the sequence of exemplary chimeric chemokines.

DETAILED DESCRIPTION

Figure 1:
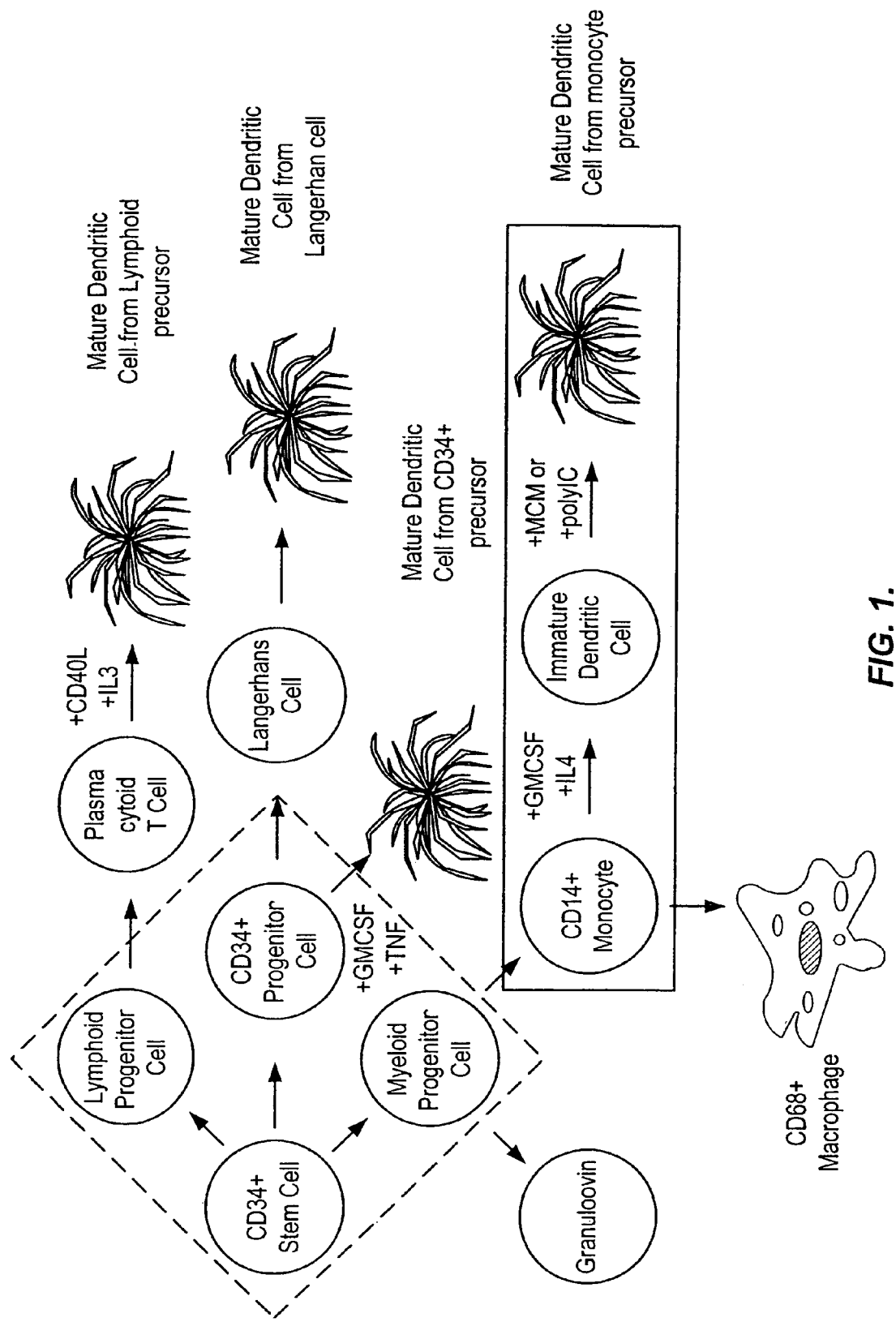
FIG. 1 shows developmental pathways of dendritic cells.

Definitions and Abbreviations
Polynucleotide
A polynucleotide refers to a deoxyribonucleotide (DNA) or ribonucleotide (RNA) in either single- or double-stranded form, and encompasses known analogs of natural nucleotides that can function in a manner similar to the naturally occurring nucleotides. The phrase "polynucleotide encoding" refers to a nucleic acid sequence that directs the expression of a specific protein or peptide. The nucleic acid sequences include both the DNA sequence that is transcribed into RNA and the RNA sequence that is translated into the protein. The nucleic acid sequence includes both the full-length nucleic acid sequence as well as non-full length sequences derived from the full-length sequence.

Subject
A is a mammal such as human patient or volunteer, an animal such as a non-human primate, rat, mouse, rodent, rabbit, and the like, an agriculturally important mammal including without limitation, a goat, pig, cow, sheep, horse, mink, and fox and the like, and pets such as dogs, cats, and the like.

Control Sequences
Control sequences are DNA sequences that enable the expression of an operably-linked coding sequence in a particular host organism. Prokaryotic control sequences include promoters, operator sequences, and ribosome binding sites. Eukaryotic cells utilize promoters, polyadenylation signals and enhancers.

Operably-linked
Nucleic acid is operably-linked when it is placed into a functional relationship with another nucleic acid sequence. For example, a promoter or enhancer is operably-linked to a coding sequence if it affects the transcription of the sequence, or a ribosome-binding site is operably-linked to a coding sequence if positioned to facilitate translation. Generally, "operably-linked" means that the DNA sequences being linked are contiguous, and, in the case of a secretory leader, contiguous and in reading phase. However, enhancers do not have to be contiguous. Linking is accomplished by conventional recombinant DNA methods.

Isolated Nucleic Acids
An isolated nucleic acid molecule is purified from the setting in which it is found in nature and is separated from at least one contaminant nucleic acid molecule. Isolated APC chemotaxin polynucleotides are distinguished from the specific APC chemotaxin polynucleotide as it exists in cells.

However, an isolated APC chemotaxin polynucleotide includes APC chemotaxin polynucleotides contained in cells that ordinarily express the APC chemotaxin polypeptide where, for example, the nucleic acid molecule is in a chromosomal location different from that of natural cells.

Purified Polypeptide
An "isolated" or "purified" polypeptide, protein or biologically active fragment is separated and/or recovered from a component of its natural environment When the molecule is a purified polypeptide, the polypeptide will be purified (1) to obtain at least 15 residues of N-terminal or internal amino acid sequence using a sequenator, or (2) to homogeneity by SDS-PAGE under non-reducing or reducing conditions using Coomassie blue or silver stain. Isolated polypeptides include those expressed heterologously in genetically engineered cells or expressed in vitro since at least one component of the APC chemotaxin polypeptide natural environment will not be present. Ordinarily, isolated polypeptides are prepared by at least one purification step.

Contaminant components include materials that would typically interfere with diagnostic or therapeutic uses for the polypeptide and may include enzymes, hormones and other proteinaceous or non-proteinaceous materials. Preferably, the polypeptide is purified to a sufficient degree to obtain at least 15 residues of N-terminal or internal amino acid sequence. To be substantially isolated, preparations have less than 30% by dry weight of non-APC chemotaxin contaminating material (contaminants), more preferably less than 20%, 10% and most preferably less than 5% contaminants. An isolated, recombinantly-produced APC chemotaxin polypeptide or biologically active portion is preferably substantially free of culture medium, i.e., culture medium represents less than 20%, more preferably less than about 10%, and most preferably less than about 5% of the volume of the APC chemotaxin polypeptide preparation. Examples of contaminants include cell debris, culture media, and substances used and produced during in vitro synthesis of APC chemotaxin polypeptide.

Of course, polypeptides and fragments of interest can be produced by any method well known in the art, such as by expression via vectors such as bacteria, viruses and eukaryotic cells. In addition, in vitro synthesis, such as peptide synthesis, may be also used.

Active Polypeptide
An active, e.g., APC chemotaxin polypeptide or, e.g., APC chemotaxin polypeptide fragment, retains a biological and/or an immunological activity similar, but not necessarily identical, to an activity of a naturally-occuring (wild-type) APC chemotaxin polypeptide. Immunological activity, in the context of this immediate discussion of the polypeptide per se, and not an actual biological role for APC chemotaxin in eliciting or enhancing an immune response, refers to an aspect of an APC chemotaxin polypeptide in that a specific antibody against an antigenic epitope possessed by a native APC chemotaxin polypeptide binds an APC chemotaxin; biological activity refers to a function, either inhibitory or stimulatory, caused by a native APC chemotaxin polypeptide. A biological activity of APC chemotaxin polypeptide includes, for example, chemotaxis, inducing, enhancing or aiding an immune response. A particular biological assay (see Examples), with or without dose dependency, can be used to determine APC chemotaxin activity. A nucleic acid fragment encoding a biologically-active portion of APC chemotaxin can be prepared by isolating a polynucleotide sequence that encodes a polypeptide having an APC chemotaxin biological activity, expressing the encoded portion of APC chemotaxin (e.g., by recombinant expression in vitro) and assessing the activity of the encoded portion of APC chemotaxin polypeptide.

In general, an APC chemotaxin polypeptide variant that preserves APC chemotaxin polypeptide-like function and includes any variant in which residues at a particular position in the sequence have been substituted by other amino acids, and further includes the possibility of inserting an additional residue or residues between two residues of the parent protein as well as the possibility of deleting one or more residues from the parent sequence. Any amino acid substitution, insertion, or deletion is encompassed by the invention. In favorable circumstances, the substitution is a conservative substitution as defined above.

"APC chemotaxin polypeptide variant" means an active APC chemotaxin polypeptide having at least: (1) about 70% amino acid sequence identity with a full-length native sequence APC chemotaxin polypeptide sequence, (2) an APC chemotaxin polypeptide sequence lacking the signal peptide, (3) an extracellular domain of an APC chemotaxin polypeptide polypeptide, with or without the signal peptide, or (4) any other fragment of a full-length APC chemotaxin polypeptide sequence. For example, APC chemotaxin polypeptide variants include APC chemotaxin polypeptide polypeptides wherein one or more amino acid residues are added or deleted at the N- or C-terminus of the full-length native amino acid sequence. An APC chemotaxin polypeptide variant will have at least about 70% amino acid sequence identity, preferably at least about 71% amino acid sequence identity, more preferably at least about 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% amino acid sequence identity and most preferably at least about 99% amino acid sequence identity with a full-length native sequence APC chemotaxin polypeptide sequence. An APC chemotaxin polypeptide variant may have a sequence lacking the signal peptide, an extracellular domain of an APC chemotaxin polypeptide polypeptide, with or without the signal peptide, or any other fragment of a full-length APC chemotaxin polypeptide sequence. Ordinarily, APC chemotaxin variant polypeptides are at least about 10 amino acids in length, often at least about 20 amino acids in length, more often at least about 30, 40, 50, 60, 70, 80, 90, 100, 150, 200, or 300 amino acids in length, or more.

"Percent (%) amino acid sequence identity" is defined as the percentage of amino acid residues that are identical with amino acid residues in an APC chemotaxin polypeptide sequence in a candidate sequence when the two sequences are aligned. To determine % amino acid identity, sequences are aligned and if necessary, gaps are introduced to achieve the maximum % sequence identity; conservative substitutions are not considered as part of the sequence identity. Optimal alignment of sequences for comparison can be conducted, e.g., by the local homology algorithm of Smith & Waterman, 1981, *Adv. Appl. Math.* 2:482, by the homology alignment algorithm of Needleman & Wunsch, 1970, *J. Mol. Biol.* 48:443, by the search for similarity method of Pearson & Lipman, 1988, *Proc. Natl. Acad. Sci. USA* 85:2444, by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., supra). Each of these references and algorithms is incorporated by reference herein in its entirety. When using any of the aforementioned algorithms, the default parameters for "Window" length, gap penalty, etc., are used.

When amino acid sequences are aligned, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) can be calculated as:

% amino acid sequence identity=X/Y·100 where

X is the number of amino acid residues scored as identical matches by the sequence alignment program's or algorithm's alignment of A and B and Y is the total number of amino acid residues in B.

If the length of amino acid sequence A is not equal to the length of amino acid sequence B, the % amino acid sequence identity of A to B will not equal the % amino acid sequence identity of B to A.

One example of an algorithm that is suitable for determining percent sequence identity and sequence similarity is the BLAST algorithm, which is described in Altschul et al., 1990, *J. Mol. Biol.* 215:403-410. Software for performing BLAST analyses is publicly available through the National Center for Biotechnology Information.

This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Extension of the word hits in each direction are halted when:c the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLAST program uses as defaults a word length (W) of 11, the BLOSUM62 scoring matrix (see Henikoff & Henikoff, 1989, *Proc. Natl. Acad. Sci. USA* 89:10915) alignments (B) of 50, expectation (E) of 10, M=5, N=-4, and a comparison of both strands.

Substantially Pure Cell Population

As used herein, a cell sample or cell population is "substantially pure" or "substantially purified" if at least about 75%, preferably at least about 85%, often at least about 90%, at least about 95% or more of the total cells in the sample are of a defined type (e.g., in a substantially pure preparation of dendritic cells, at least about, e.g., 95% of the total number of cells are dendritic cells, while in a substantially pure preparation of immature dendritic cells, at least about, e.g., 95% of the total number of cells are immature dendritic cells.

Allogeneic and Autologous Cells

An allogeneic cell means a cell that is derived from individuals of the same species that is sufficiently unlike genetically to interact antigenically. An autologous cell means a cell that occurs normally in a tissue or body structure, referring to a cell in which the donor and recipient of the cell are the same individual.

Abbreviations

When referring to a chemokine "h" means human and "m" means murine. In some cases, Latin letters are used instead of the Greek α, β, or γ. Thus, as used herein, mMIP-1a means murine MIP-1α.

APC Chemotaxin Compositions

In one aspect, the method of the invention involves administering a composition that contains an agent that is chemotactic for dendritic cells (DCs) and/or macrophages (together referred to as "antigen-presenting cells" or "APCs"). For convenience, the chemotactic agent is sometimes referred to as a "APC chemotaxin," and the composition containing the APC chemotaxin (which may contain excipients or other components) is sometimes referred to herein as "the chemotactic composition" or "the composition."

In some embodiments of the invention, the APC chemotaxin is specifically chemotactic for specified cell types (e.g., dendritic cells) or cell developmental stages (e.g., immature dendritic cells). In related embodiments the agent, while chemotactic for some cells, is not chemotactic for certain cell-types (e.g., neutrophils) or cell developmental stages (e.g., mature dendritic cells). Chemotaxis is determined using one or more of the assays described herein.

In one aspect, the methods of the invention involve administration of an antigen, in addition to a chemotactic composition. Thus, in one embodiment, the chemotactic composition and an antigen are administered at the same physical site in the subject. For example, the antigen may be combined with a chemotactic composition, and the mixture administered (e.g., injected) together. Alternatively, the composition and the antigen are administered separately to the same area of the subject (e.g., injected to the same site, applied topically to the same site, and the like). In some embodiments, as described in detail infra, the composition and antigen are administered at different times.

Without intending to be bound by a particular mechanism, it is believed that the APC chemotaxin(s) promote(s) an immune reaction to the antigen by recruiting APCs to areas of antigen contact. Antigens are taken up by APCs and partially degraded. Subsequently, a fraction of the degraded antigen is presented with MHC class I or II molecules on the surface of the APC. Such cells stimulate proliferation of either cytotoxic T cells or helper T cells, or the production of antibody by B cells.

In a related aspect of the invention, the chemotactic composition is administered without an accompanying antigen (e.g., injection into a solid tumor to elicit an immune response to cancer cells, or injection in tissue surrounding a solid tumor, e.g. within 2 cm, of a solid tumor). Without intending to be bound by a particular mechanism, it is believed that the APC chemotaxin(s) promote(s) an immune reaction to the endogenous (e.g. tumor) antigen by recruiting APCs to areas of antigen contact.

The invention also provides new methods and reagents useful for therapeutic and prophylactic immunization (i.e., the deliberate provocation, enhancement or intensification, of an adaptive immune response). Particular advantages expected over prior immunization methods include:

(1) an accelerated immune response in a host following administration of antigen, (2) a more effective response to administration of, or exposure to, very small quantities of an antigen (e.g., toxin or pathogen) due to increased antigen uptake by APCs, and (3) more effective anti-tumor therapies (e.g., due to enhanced tumor antigen uptake by host APCs).

As used herein, an "immune response" means, unless otherwise specified, an adaptive immune response to a specific antigen. In one aspect, an immune response involves the concerted action of lymphocytes, antigen presenting cells, phagocytic cells, and various soluble macromolecules in defending the body against infection or other exposure to non-self molecules. The immune response can be detected and quantified (e.g., following immunization) by measuring cellular or humoral responses according to numerous assays known in the art (see, e.g., Coligan et al., 1991 (suppl. 1999), *Current Protocols in Immunology*, John Wiley & Sons (hereinafter, sometimes "Coligan")). For example, to detect a cellular immune response, T cell effector effects against cells expressing the antigen are detected using standard assays, e.g., target-cell killing, macrophage activation, B-cell activation or lymphokine production. Humoral responses are measured by detecting the appearance or increase in the titer of antigen-specific antibodies using routine methods such as ELISA. The progress of the antibody response can be determined by measuring class switching (i.e., the switch from an early IgM response to a later IgG response. To enhance an immune response means, unless otherwise specified, to increase the vigor and/or magnitude and/or quality of the immune system being stimulated. For example, the early appearance and/or a high titer of antigen-specific antibodies, especially when compared to controls in which the immune response was not modulated, signifies (but does not limit the invention) a vigorous (enhanced) immune response. Preferably, such magnitude is at least 2-fold, more preferably 3-fold, 4-fold, 5-fold, 6-fold, 7-fold, 8-fold, 9-fold and most preferably at least 10-fold when compared to control cells in which the immune response was not modulated. An enhanced immune response also includes enhancing the immune response's quality, such as can be determine, for example that is meant to be non-limiting, higher affinity antibodies to the specific antigen, a greater presence of preferred IgGs, etc.

Chemotactic Compositions

According to the invention, a composition comprising an APC chemotaxin is administered to induce or enhance an immune response in a subject. In various embodiments, the chemotaxin attracts dendritic cells, macrophages, or both. Chemotaxins that attract dendritic cells, particularly immature dendritic cells, are especially useful. In a particularly useful embodiment, the chemotaxin has a high level of specificity for a particular cell type, developmental stage, or both. Thus, in one embodiment, the APC chemotaxin attracts immature dendritic cells, but does not attract one or more of the following other classes of cells: mature dendritic cells, neutrophils, monocytes, T cells, B cells, eosinophils, mast cells, red blood cells, and progenitor cells.

The APC chemotaxins of the invention may be any of a large variety of compounds, both naturally occurring and synthetic, organic and inorganic, and including polymers (e.g., oligopeptides, polypeptides, oligonucleotides, and polynucleotides), small molecules, antibodies, sugars, fatty acids, nucleotides and nucleotide analogs, analogs of naturally occurring structures (e.g., peptide mimetics, nucleic acid analogs, and the like), and numerous other compounds. In a preferred embodiment, the chemotactic compositions comprise polypeptides, such as naturally occurring chemokines, polypeptide variants, or mimetics of chemokines. In a preferred embodiment of the invention, the composition contains at least a chemokine polypeptide, such as hMCP2, hMCP3, hMIP1β, hMIP3α, hMIP3β, mMIG, mMIP1γ, mMDC, vMIP1, mC10, a variant of an aforementioned chemokine, such as a recombinant polypeptide produced by in vitro mutation, in vitro recombination or shuffling of a polynucleotide encoding the chemokines, a polynucleotide encoding at least one of the aforementioned chemokines or variant molecules, or a synthetic (i.e., chemically synthesized) polypeptide variant (e.g., mimetic) of one or more of these chemokines.

Reagents and methods for, inter alia, identifying APC chemotaxins, and preparing and administering the compositions of the invention are described infra.

Practising the Invention

Assays for Identification of APC Chemotaxins

In one aspect of the invention, APC chemotaxins are identified using in vivo or in vitro assays.

(a) In vitro Assays

The APC chemotaxins used in the methods of the invention have certain properties, which can be detected in in vitro chemotaxis assays. In vitro chemotaxis assays are well known. Migration assays are often carried out by physically separating the cells from the chemoattractant using a porous membrane and allowing the cells to move directionally, up a diffusion gradient of the chemotaxin (see, e.g., Keller, 1972, *Agents Actions* 2:161-69; Gee A. P., 1984, *Mol. Cell. Biochem.* 62:5-11; Keller et al., 1974, *Antibiot. Chemother.* 19:112-25).

A variety of assay configurations are known and are suitable in the practice of the present invention. Most often, standard filter based assays are used because they are convenient, robust, and relatively inexpensive. These filter based assays include a classical or modified Boyden chamber and variants (see, e.g., Bozarth et al., 1997, *Meth. Cell Science*, 19:179-187; Frevert et al., 1998, *J. Imm. Methods*, 213:41-52; Penno et al., 1997, *Meth. Cell Science*, 19:189-195; O'Leary et al., 1997, *Am. J. Resp. Cell and Mol. Bio.*, 16:267-274; Falk, et al., 1980, *J. Imm. Methods*, 33:239-247; Harvath, et al., 1980, *J. Imm. Methods*, 37:3945; Richards et al., 1984, *Immunological Communications*, 13:49-62; Falk et al., 1982, *Infection and Immunity* 36:450-454; Harvath et al., 1982, *Infection and Immunity* 36:443-449; all incorporated by reference). In filter-based assays, cells are placed in a compartment separated from a candidate chemotaxin by a filter through which the candidate chemotaxin can diffuse. After an incubation period, the number of cells (or percentage of total cells) that have migrated onto or through the filter is determined. Migration of cells at a level above background, i.e., migration in the absence of the candidate chemotaxin, e.g., in the presence of only a carrier such as PBS or Chemotaxis buffer (infra), indicates that the candidate chemotaxin is indeed chemotactic for the target cell type. Conversely, when the number of migrating cells is at or below background, the candidate chemotaxin is considered not chemotactic for the target cell type.

One suitable apparatus for carrying out in vitro chemotaxis assays is a 96-well ChemoTx® microplates (Neuroprobe Inc.; Gaithersburg, Md.). The ChemoTx® instrument has a 96 well microplate of injection-molded, tissue-culture grade, transparent polystyrene. The microplate provides bottom wells for chemoattractants and other reagents. In place of top "wells," a framed filter is used that confines each cell-suspension sample to its site on top of the filter. The 96 sites on the filter correspond to the 96 wells in the microplate, and cell suspension pipetted directly onto the sites on the top side of the filter sit in hemispherical drops during incubation. After incubation the migrated cells on the filter and in the microplate are counted. (U.S. Pat. No. 5,284,753 (incorporated herein by reference in its entirety for all purposes)).

To assay for chemotactic activity using an apparatus such as the ChemoTx® microplates apparatus, candidate chemotaxins are added to lower wells (e.g., about 30 microliters) at one or more concentrations (e.g., about 1 nM, about 10 nM, about 100 nM, about 10 ng/ml, about 100 ng/ml and/or about 1 μg/ml), and cells are placed on porous polycarbonate filters positioned above the chemotaxin solution in each well. The filters have a pore size of about 3 μm, or about 5 μm, so that only cells exposed to an agent chemotactic for the cell will migrate into and/or through the filter. In the microplate configuration, about 20 μl of cells (at about $1 \times 10^6$ to about $1 \times 10^7$ cells per ml, e.g., $5 \times 10^6$ cells per ml) are usually used. The cells are incubated for a period of time (e.g., 0.5 to 6 hours, usually about 1.5 h, at from about 22° C. to about 39° C., usually 37° C.).

When in vitro assays are conducted using a purified cell population (e.g., dendritic cells, neutrophils, immature dendritic cells, etc.) the assay conditions are usually tailored to the cell type being studied. For example, cells that are relatively plastic are able to crawl through certain filters, where as others become "stuck" in the filter. Thus, monocytes exposed to a monocyte chemotactic agent migrate through a 5 μm filter into the lower chamber. In contrast, immature or mature dendritic cells exposed to a chemotactic agent migrate into, and are retained in, a 3 μm or 5 μm filter. Therefore, the choice of migration assay format and the method of quantification can vary depending on the type of cells studied. For example, a 5 μm pore size is usually used for a monocyte migration assay; the assay is typically carried out for 90 minutes, and the migrating cells (if any) are detected in the well. For mature dendritic cells, a 3 μm pore size filter and 90 minutes incubation are used, and the cells are detected in the filter. These and other exemplary assay conditions are shown in Table 1. However, it will be appreciated that a number of different assay formats and conditions can be used to determine that an agent does (or does not) have chemotactic activity (e.g., for a particular cell). Table 1 also provides exemplary positive and negative controls for use in assays. Positive controls are agents that, when used at 100 nM concentration, have chemotactic activity. Negative controls are agents that, when used at 100 nM concentration, do not have chemotactic activity.

TABLE 1

Exemplary assay parameters and positive and negative controls for in vitro chemotaxis assays

| cell type | filter (pore size) | time (minutes) | location | +con. | −con. |
|---|---|---|---|---|---|
| monocyte | 5 μm | 90 | well | RANTES | MIP1b |
| immDC | 5 μm | 90 | filter | RANTES | SLC |
| matDC | 3 μm | 90 | filter | SLC | RANTES |
| neutro | 3 μm | 60 | well | IL8 | SLC |
| eosino | 3 μm | 60 | well | Eotaxin | IL8 |
| T cell | 3 μm | 180 | well | MDC | Eotaxin |
| B cell | 3 μm | 180 | well | SLC | Eotaxin |
| Macrophage | 5 μm | 90 | filter (+well) | RANTES | SLC |

Key:
+con. (positive control), −con. (negative control) are used at 100 nM concentrations.

To determine the number of cells that have migrated in the presence of an agent, a variety of methods can be applied. To assay cells (e.g., dendritic cells) that are caught in a filter, the filters are scraped to remove nonadherent cells (i.e., cells that have simply settled onto the top side of the filter), and the cells that have moved into the filter or adhered to its lower surface are quantitated. For cells that migrate through the filter (e.g., monocytes), the filter can be discarded, and the number of cells that have migrated through the filter into the "lower" (chemotaxin-containing chambers and control chambers) is determined. Suitable cell quantitation methods are well known and include direct (microscopic) counting of migrated cells, histological, cytochemical, immunofluorescence (using antibodies to cell-specific or stage-specific markers), in situ staining methods, use of radiolabled cells, and assays for RNA or DNA content (e.g., using reagents such CyQuant, Molecular Probes, Eugene Oreg., e.g., on a lysed cell extract), protein content (e.g., using stains such as Hema3), enzyme activity (e.g., β-glucuronidase), and the like. Often it is convenient to select stains that can be detected using densitometric or fluorescence plate readers.

In some embodiments, several concentrations of the candidate chemotaxin are used to detect an active concentration, e.g., at least two, typically at least three different concentrations, over a range of at least 10-fold, typically at least 100-fold, frequently at least 1,000-fold, and often at least 10,000-fold differences.

The chemotaxis assays can be carried out using a heterogeneous mixture of cells (e.g., peripheral blood mononuclear cells (PBMCs)) or a purified subpopulation (e.g., immature DCs, mature DCs, neutrophils, monocytes and the like) or tissue culture cells derived from a certain cell type and with characteristics of those cells (e.g., THP1 (an acute monocytic leukemia cell line), CEM acute lyphoblastic leukemia, T lymphoblast cell line). When a heterogeneous mixture of cells is used, the cell type or developmental stage of migrating cells is usually determined (e.g., based on morphology, histology, or staining specific markers). When homogeneous cell preparations (e.g., substantially purified neutrophils), are used, any cells that migrate to the chemotaxin can be presumed to be of that type.

In various embodiments, a candidate chemotaxin is considered chemotactic for a particular cell type if the candidate chemotaxin, at a concentration about between about 1 pM and about 1 μm, e.g., between about 1 nM and 500 nM, e.g., 1 nM, about 10 nM, about 100 nM, or between about 1 pg/ml and about 10 μg/ml, e.g., between about 1 ng/ml and 1 μg/ml, e.g., about 10 ng/ml, about 100 ng/ml or about 1 μg/ml, attracts the cell at least 2-fold, preferably at least 4-fold, and often at least 8-fold more than "chemotaxis buffer" (a negative control) in an in vitro assay. Chemotaxis buffer is 0.1% BSA (Sigma; St. Louis, Mo.) in Hank's Balanced Salt Solution (HBSS; Life Technologies; Gaithersburg, Md.; $CaCl_2$ (0.14 g/l), KCl (0.4 g/l), $KH_2PO_4$ (0.06 g/l), $MgCl_2$-$6H_2O$ (0.1 g/l), $MgSO_2$-$7H_2O$ (0.1 g/l), NaCl (8 g/l), $NaHCO_3$ (0.3 g/l), $Na_2HPO_4$ (0.048 g/l), D-glucose (1 g/l)), with 1.4 mM $Ca^{++}$ and 1 mM $Mg^{++}$. An alternative negative control is PBS. A candidate chemotaxin is considered not to be chemotactic for a cell type if the candidate chemotaxin at a concentration of 1 nM, 10 nM, 100 nM, or 10 ng/ml, 100 ng/ml or 1 μg/ml, does not attract more cells (e.g., at least as many, sometimes at least 1.5-fold as many) as the negative control in an in vitro assay. In various embodiments, a candidate chemotaxin is considered chemotactic for a particular cell type if the candidate chemotaxin, when injected in vivo, e.g., intradermally into a mouse or monkey, at 2 μg, alternatively 10 μg, often 20 μg, attracts the cell at least 2-fold, preferably at least 5-fold, and often at least 10-fold more than a negative control, such as PBS (KCl (0.2 g/l), $KH_2PO_4$ (0.2 g/l), NaCl (8.0 g/l), Na2HPO4 (2.16 g/l)). In various embodiments, a candidate chemotaxin is considered not chemotactic for a cell type if the candidate chemotaxin, when injected at 2 μg, alternatively 10 μg, often 20 μg, does not attract more cells of the type (e.g., at least as many, sometimes at least 1.5-fold as many) than the negative control in an in vivo assay.

In some embodiments, an agent is determined to be chemotactic because when having greater chemotactic activity than a known chemotaxin (e.g., known in the art or determined by the assays described herein).

Non-filter based chemotaxis assays may also be used, e.g., a cell migration assay can be carried out using a monolayer of cells grown on the filter as a barrier. In other examples, cellular motility may also be assessed by monitoring the movement of a single cell under a video microscope. In these types of experiments, the chemoattractant is applied through a capillary, and the physical distance of cell's lateral movement toward the source of the chemoattractant is recorded.

(b) In vivo Assays

In one embodiment, the chemotactic properties of an agent can be determined in animals, e.g., mammals such as non-human primates and mice, as described in Examples 2-4, infra. In one in vivo assay, the candidate chemotactic agent (e.g., 2-20 μg in PBS) is administered by intradermal injection into an animal. After a period of time (e.g., 24 hours, 72 hours, 96 hours), the animal is euthanized or a biopsy is taken. The area around the injection site is excised and subjected to routine histology or immunohistology techniques to determine the presence or absence of cell infiltration and, if an infiltrate is present, to characterize and quantitate the infiltrating cells (e.g., mononuclear cells, neutrophils, dendritic cells, etc.). For general histological methods, see, e.g., *The Manual of Histologic Staining Methods of the Armed Forces Institute of Pathology"*, by Lee G. Luna, McGraw-Hill, 3rd edition, 1968 (hereinafter "Luna"). In one embodiment, cells are characterized by preparing frozen sections and staining with cell type specific antibodies, or cell type-specific combinations of antibodies, using well known methods (see, Harlow et al., 1988, *Antibodies: A Laboratory Manual*, Cold Spring Harbor Laboratory).

Characterization of Cell Types and Preparation of Purified Cells

Enriched or substantially purified cell populations can be used in in vitro chemotaxis assays. These cell populations can be prepared by a variety of methods known in the art depending on the specific cell-type desired. Typically, substantially purified cell populations are prepared by culture under specific conditions, by physical characteristics such as behavior in a density gradient, by sorting according to characteristic markers (e.g., by fluorescence activated cell sorting (FACS) using antibodies (preferably monoclonal antibodies) to cell-surface proteins, immunoprecipitation), or other methods.

Cells can be identified by histology (see, e.g., Luna, supra), by immunological staining and similar methods (see, e.g., Harlow, supra; Coligan et al., supra). Table 2A and 2B list exemplary markers useful for characterizing or purifying (e.g., FACS) certain immune system cells. Many other markers are known in the art, both for the cells listed and for other immune system cells such as B cells, T cells, neutrophils, eosinophils, and others (see, e.g., Janeway-Travers, 1994, *ImmunoBiology* Garland Pub., N.Y.; Paul, *Fundamental Immunology* 3rd Ed, Raven Press N.Y. 1993). Table 2A shows certain classical cell surface markers; Table 2B shows certain chemokine receptors expressed by specific cell types.

TABLE 2A

Selected Cell Surface Markers

| Marker | CD3 | CD14 | CD20 | CD25 | CD68 | CD80 | CD83 | CD86 | HLA-DR | CD1a |
|---|---|---|---|---|---|---|---|---|---|---|
| Monocyte-derived Immature DCs | – | – | – | – | + | – | – | – | low | high |
| Mature DCs | – | – | – | + |  | + | + | high | high | + |
| Macrophages |  | high |  | + |  |  |  |  |  | – |
| Monocytes | – | + | – | – |  |  | – | – | low | low | – |

Key:
Table 2A shows the levels of markers as determined by staining with an antibody specific for the marker.
"–" indicates staining equivalent to an isotype control antibody (an isotype control antibody is the same isotype as the staining antibody, but does not recognize the assayed epitope);
"+" indicates at least 10 fold higher levels of staining as isotype control;
"low" indicates staining 2-5 fold higher than isotype control;
"high" indicates staining 10 to 1000 fold higher than isotype control.

TABLE 2B

Chemokine Receptor Expression Profile of Specific Cell Types

| | CC receptors | | | | | | | CXC receptors | | | | | XCR1 |
|---|---|---|---|---|---|---|---|---|---|---|---|---|---|
| | R1 | R2 | R3 | R5 | R6 | R7 | R1 | R2 | R3 | R4 | R5 | | |
| Immature DCs | + | – | – | + | – | – | – | – | – | + | – | | – |
| Mature DCs | – | – | – | – | – | + | – | – | – | + | – | | – |
| Monocytes | + | + | – | – | – | – | – | – | – | + | – | | – |

Methods for preparing substantially purified cell compositions for use in in vitro chemotaxis assays are briefly described infra and in the Examples. However, the invention does not require that any particular purification method be used, so long as the desired cells are obtained; many variations and alternative methods are known to those of skill in the art. Further, many other purification and detection methods, including methods suitable for cells not specifically listed herein, are known in the art or can be easily developed. Further, cloned cell lines derived from immune system tissues can be used in the chemotaxis assays described herein, if desired. General immunological, purification and cell culture methods are described in Coligan et al., and (1991) *Current Protocols in Immunology,* John Wiley & Sons, including supplements through 1999, incorporated herein by reference in its entirety for all purposes. Unless otherwise specified, cells in culture are incubated at 37° C. in 5% $CO_2$.

(a) Monocytes

Suitable methods for monocyte purification are found in Bender et al., 1996, *J. Immunol. Methods* 196:121-35 (also see U.S. Pat. No. 5,994,126). Briefly, monocytes are isolated from PBMC by depleting T cells using immobilized antibodies against a pan T cell surface marker CD2. Conveniently, a commercially available source of CD2 antibodies attached to magnetic beads (Dynal; Lake Success, N.Y.) is used. PBMC isolated from a buffy coat (typically 35 mls containing $400 \times 10^6$ PMBC) by conventional Ficoll gradient centrifugation methods are resuspended in MACS buffer (DPBS (HyClone; Logan, Utah) with 1% BSA (Sigma)) at $20 \times 10^6$ cells per ml. DPBS is Dulbecco's Phosphate Buffered Saline ($CaCl_2$ (0.1 g/l), KCl (0.2 g/l), $KH_2PO_4$ (0.2 g/l), $MgCl_2 \cdot 6H_2O$ (0.1 g/l), NaCl (8.0 g/l), $Na_2HPO4$ (2.16 g/l)). An appropriate amount of immobilized CD2+ magnetic beads (typically 10 µl per $10^6$ cells) are added to the cells. The mixture is incubated for 15 minutes at 4° C. with gentle rotation. The magnetically tagged T cells are removed from the unlabeled cells on a magnetic cell sorter (Dynal) according to the manufacturer's protocols. The unlabeled cells contain primarily monocytes and B cells.

B cells in the above preparation are removed by taking advantage of differential adhesion properties. Briefly, PBMC depleted of T cells are allowed to adhere to the plastic of a T-175 tissue culture flask ($100 \times 10^6$ cells/flask; Costar; Acton, Mass.) for 3 hours at 37° C. Non-adherent cells (comprising largely B cells) are aspirated. To completely remove non-adherent cells, the flasks are rinsed 3 more times with DPBS. The resulting cells are largely enriched (i.e., >90%) for monocytes.

Monocytes can also be isolated by positive selection of CD14 antigen. Briefly, PBMC isolated from peripheral blood, such as a buffy coat, by standard Ficoll gradient centrifugation methods are resuspended in MACS buffer at $1 \times 10^6$ cells/ml. Immobilized antibodies against the CD14 surface antigen, such as CD14+ magnetic microbeads (Milteyni) are added (1 µl of beads per $1 \times 10^6$ cells) and the mixture is incubated at 4° C. for 15 minutes. Monocytes are separated from the other cell populations by passing the mixture through a positive selection column on a magnetic cell sorter (Miltenyi Biotech; Auburn, Calif.) according to manufacturers protocol. Monocytes that are retained on the column are eluted with MACS buffer after the column is removed from the MACS apparatus. Cells are then pelleted by centrifugation and resuspended in RMPI plus 10% FCS media at $10^6$ cells per ml. Monocytes isolated by this method are cultured essentially the same way as those isolated by the CD2+ depletion method.

(b) Preparing Purified Dendritic Cell Populations

Suitable methods for purification of dendritic cells, including separate mature and immature populations, are known in the art. Substantially purified dendritic cells (including subpopulations of mature or immature cells) can be prepared by selective in vitro culture conditions.

Dendritic cells are widely distributed in all tissues that have contact with potential pathogens (e.g., skin, gastrointestinal and respiratory tracts, and T cell-rich areas of the secondary lymphoid tissues). In the skin and upper respiratory tract they form a lattice of highly arborised cells (called Langerhans cells in the skin). After capturing antigen, dendritic cells in the peripheral tissues such as the skin and gut, traffic via the draining lymphatics to the T cell areas of lymph nodes where they present the internalized antigen. Immature dendritic cells function to take up and process antigens. During subsequent migration to the draining lymph node, the DC matures. The mature dendritic cells functions as the key APC to initiate immune responses by inducing the proliferation of pathogen specific cytotoxic and helper T cells.

Substantially pure populations of dendritic cells can be produced by in vitro culture, infra). In addition, there are marked changes in expression of chemokine receptors during dendritic cell maturation which can be used to identify cell stage (Campbell et al., 1998, *J. Cell Biol* 141:1053; Chan et al., 1999, *Blood* 93:3610; Dieu et al., 1998, *J. Exp Med* 188:373; Kellermann et al., 1999, *J. Immunol* 162: 3859). For example, immature dendritic cells express predominately CCR1, CCR5, and CXCR4. Upon maturation, these receptors, with the exception of CXCR4, are down regulated (See also, Table 2B).

In culture, immature forms of dendritic cells undergo maturation thought to be analogous to the events during migration of dendritic cells from the point of antigen contact until to the secondary lymphoid tissues. Human or macaque dendritic cells of various developmental stages can be generated in culture, from $CD14^+$ blood progenitors using specific cytokines. A separate lineage of dendritic cells can be differentiated from CD34+ precursor cells from cord blood or bone marrow. In one embodiment of the invention, subpopulations of dendritic cells are generated for in vitro assays for identification of chemotactic compositions (i.e. to assess chemotaxin potency and selectivity against defined DC sub-types). Exemplary subpopulations of dendritic cells are: (1) immature peripheral blood monocyte derived cells; (2) mature peripheral blood monocyte derived cells, and (3) cells derived from CD34+ precursors. Subpopulations are isolated or produced by a variety of methods known in the art. For example, immature and mature dendritic cells from PBMCs are produced according to Bender et al. supra.

(i) Immature Dendritic Cells

Briefly, PBMCs are depleted of T cells using immobilized antibodies against the cell surface marker CD2 (present on all T cells). Commercially available CD2+ dynabeads (Dynal) can be used according to manufacturer's protocol. The T-cell depleted mixture is separated into adherent versus non-adherent fractions by incubating the cells on tissue culture grade plastic for 3 hours at 37° C. Non-adherent cells are gently removed, and adherent cells (generally CD14+ monocytes) are placed in culture media (e.g., RMPI+10% FCS) supplemented with 1000 U/mL each of GM-CSF and IL-4 (R&D Systems, Minneapolis, Minn.) ("Day 1"). Between days 3-7 the cells begin to display a veiled morphology, and cytokines are replenished on days 2, 4, and 6, at which time the cells can be harvested as immature dendritic cells. In one embodiment, cells of this in vitro stage are isolated and used in the assay. Approximately $10 \times 10^6$ dendritic cells are typically obtained from $400 \times 10^6$ PBMCs.

Day 7 immature dendritic cells exhibit typical dendritic cell morphology, with elongated cell body and many processes. The size of the cells increase significantly compared to the precursor monocytes. Immature dendritic cells can be characterized phenotypically by monitoring their expression of cell surface markers.

(ii) Mature Dendritic Cells

Immature dendritic cells (generated from peripheral blood monocytes or from bone marrow derived CD34+ precursors) can be further activated and differentiated to become mature dendritic cells. Two methods are primarily used: MCM (macrophage conditioned medium) and double-stranded RNA-ploy (I:C) stimulation (Celia et al, 1999, *J Exp Med*. 189:821-9; Verdijk et al., 1999, *J Immunol*. 1999 1:57-61).

In the MCM method, day 6 immature dendritic cells are harvested by centrifugation and resuspended in at $10^6$ cells/ml in maturation medium (e.g., MCM diluted (up to 1:1 with RPMI containing 10% FCS). GM-CSF (1000 U/ml) and IL-4 (1000 U/ml) are added. Cells are cultured for three more days, without further addition of GM-CSF (1000 U/ml) and IL-4. Day 9 cells are used as mature dendritic cells.

In the poly (I:C) method, day 6 immature dendritic cells are harvested and resuspended in the standard culture medium (RPMI plus 10% FCS) supplemented with 20 µg/ml of poly (I:C) (Sigma), 1000 U/ml of GM-CSF and IL-4. Cells are cultured for another three days without additional cytokines. Day 9 cells are used as mature dendritic cells.

Mature dendritic cells generated by these two different methods exhibit phenotypic and functional properties distinct from those of immature dendritic cells or the precursor monocytes (See Table 2A). Mature dendritic cells from each preparation are thoroughly characterized by FACS to ensure that the desirable cell types are obtained.

Notably, generated mature dendritic cells express significantly higher level of MHC class II on the cell surface than immature cells. Expression of CD80, CD83 and CD86 are also up-regulated. Chemokine receptor expression also changes dramatically during the maturation process. For instance, CCR1, CCR5 are down-regulated sharply in mature cells, while CCR7 is up-regulated and appears on the cell surface within a few hours after addition of MCM. Functionally, mature dendritic cells are no longer capable of efficiently taking up antigen, but gain the ability to stimulate the proliferation of naive T cells and B cells. Mature dendritic cells also change their migratory behaviors; they no longer respond to ligands for CCR1, CCR2 and CCR5, such as MIP-1α, RANTES and MIP-1β. Instead, they respond to CCR7 ligands SLC and ELC.

MCM Media

MCM is prepared by as described by Romani et al., 1996, *J. Immunol. Methods* 196:137) with minor modifications. Briefly, petri dishes (100 mm, Falcon) are coated with 5 ml of human Ig (10 mg/mL) for 30 min at 37° C. and washed with PBS 2-3 times immediately before use. $50 \times 10^6$ PBMC in 8 ml are layered onto human Ig-coated plates for 1-2 hours. Non-adherent cells are washed away and discarded. The adherent cells are incubated in fresh complete medium (RPMI+10% normal human serum) at 37° C., and the resulting media MCM) is collected after 24 hours. The TNF-α concentration in the MCM is determined by the standard ELISA method (e.g., using a TNF-α ELISA kit (R&D Systems, Minneapolis, Minn.)). The final TNF-α, level in MCM is adjusted to 50 U/ml by mixing an appropriate amount of MCM with RPMI/10% fetal calf serum.

(c) Neutrophils

Suitable methods for neutrophil purification are known in the art. According to one suitable method, whole fresh blood (WB) is diluted 1:1 with 3% dextran in a 50 ml centrifuge tube and allowed to sediment for 30-45 minutes at room temperature. Twenty-five ml of WB plus 25 ml dextran results in approximately 35 ml of supernatant after 30 minutes sedimentation. The supernatant is layered over 12-15 ml Ficoll and centrifuged at 400× g for 3040 minutes at 18-20° C. The plasma/platelet layer containing mononuclear cells and Ficoll-Paque are removed by aspiration. Neutrophils are found in the white layer above the erythrocyte (RBC) layer. (In some preparations, the neutrophil and erythrocyte layers are mixed. In these cases, RBCs are removed by hypotonic lysis: 12.5 ml of cold 0.2% NaCl is added to the neutrophils/RBC pellet while vortexing. 12.5 ml of cold 1.6% NaCl is immediately added while still vortexing. The cells are centrifuged at 60-100× g for 10 m and recovered. If necessary the lysis step is repeated). The resulting neutrophils are >95% pure (with the eosinophis as the primary remaining cells).

(d) Macrophages

Suitable methods for purification of macrophages are known in the art. One suitable method is described in Paluka et al. (1998) *J Imm.* 9:4587-95, which is incorporated by reference herein in its entirety for all purposes.

(e) T Cells

Suitable methods for purification of T cells are known in the art. T lymphocytes are routinely prepared by removal of monocytes from the PBMC prepared by standard Ficoll gradient centrifugation methods (Coligan, supra). Monocytes are removed by allowing PMBC to adhere to tissue culture flasks. The non-adherent cells (lymphocytes) are cultured in RPMI/10% FCS in the presence of PHA (5 µg/ml) and human recombinant IL-2 (20 ng/ml) for two weeks, and the cells are harvested.

(f) B Cells

Suitable methods for purification of B cells are known in the art. Highly purified B cell populations are isolated by negative selection with sequential depletion of monocytes/natural killer (NK) cells and T cells (as described in *Current Protocols in Immunology*, supra). Depletion of monocytes and NK cells are carried out by using L-leucine methyl ester (L-LME). Briefly, PBMC isolated from peripheral blood (e.g., from a buffy coat) by standard Ficol gradient methods are resuspended at $3 \times 10^6$ cells/ml in PBS. Freshly prepared L-LME (0.05 M solution in RPMI, no serum) is added to cells at 1:10 dilution (5 mM final). The mixture is incubated for 35 minutes at room temperature, the cells are pelleted by centrifugation, followed by washing 3× with PBS. T cells are further depleted by rosetting with neuromimidase-treated sheep red blood cells (NSRBC): cells are adjusted to $10^7$ cells/ml in RPMI/10% FCS. Five ml of cells are transferred into a 50 ml centrifuge tube. Then, 2.5 ml of fetal calf serum and 2.5 ml of NSRBC are added to the tube. The mixture is incubated for 10 minutes at 37° C. The cells are then centrifuged at 150× g at room temperature for 10 minutes to pellet the cells and promote rosette formation. The mixture is incubated at 4° C. for 2 hours. The pellet is gently resuspended, and the cell suspension is underlaid with Ficol (10 ml). The tube is centrifuged at 400× g for 25 minutes. B cells in the interface are removed, pelletted and washed three times with HBSS. After repeating the rosetting step, B cells are resuspended in RPMI/10% FCS for migration assays.

(g) Eosinophils

Suitable methods for purification of eosinophils are known in the art. One method for preparation of substantially purified eosinophils is by further isolation from the preparation described in the neutrophil isolation protocol, supra. Separation of eosinophils from neutrophils is achieved by a negative selection method, where immobilized antibodies against the CD16 surface antigen are used to deplete the CD16 positive neutrophils. Briefly, the neutrophil preparation is resuspended in MACS buffer (1% BSA in DPBS) at a density of $10^6$ cells/µl. An equal volume of CD16+ microbeads (CD16 immobilized on magnetic spheres; Miltenyi Biotech; Auburn, Calif.) is mixed with the cells. The mixture is incubated at 4° C. with gentle shaking for 30 minutes. Cells are then passed through a negative selection column to remove the magnetically labeled neutrophils (CS column, Miltenyi Biotech; Auburn, Calif.) LC, Miltenyi) and the column is washed with one column volume of MACs buffer. The flow-through and wash fractions contain eosinophils and are combined. Eosinophils isolated by this method are more than 95% pure (as determined by FACS, e.g., for the presence of the CD16+ cells).

Chemokines as Chemotactic Compositions

The APC chemotaxins of the invention may be any of a number of types of compounds. Often, the chemotaxin is a polypeptide, such as a chemokine, or a protein mimetic. Thus, in an embodiment, the chemotactic composition comprises one or more chemokines, chemokine analogues, or chemokine-encoding polynucleotides.

Chemokines are protein hormones that, among other activities, direct trafficking of white blood cell populations, e.g., in the primary lymphoid organs, blood, tissues, secondary lymphoid organs, lymph, and (in some instances), back into circulation. Over 50 distinct chemokines have been identified to date in humans, and numerous chemokines from other mammals and chemokines encoded by mammalian viruses are known.

Structurally, known chemokines are divided into four classes: CC, CXC, C, and CX3C, based on the number and spacing of the amino-terminal cysteine residues in a conserved structural motif. Chemokines exert promigratory effects by binding to an array of cell surface receptors on the surface of target leukocytes. Known receptors are of the seven transmembrane spanning, G protein coupled receptor (7TM GPCR) class. Of the almost 20 human chemokines receptors characterized (i.e., those receptors for which a ligand has been identified and binding and/or signaling events are well characterized), nine are CC chemokine receptors (CCR), six are CXC chemokine receptors (CXCR), one is a CX3C chemokine receptor (CX3CR), and one is a C chemokine receptor (provisionally 'XCR'). In addition, one promiscuous chemokine receptor of broad binding specificity, originally known as the Duffy blood group antigen (Duffy Ag, sometimes denoted 'DARC') is known.

Chemokine proteins can be obtained from suppliers, e.g., R&D Systems (Minneapolis, Minn.), or may be prepared using routine techniques based on published sequences (e.g., as described in Sambrook et al., 1989, *Molecular Cloning: A Laboratory Manual*, (2nd ed.) Vols. 1-3, Cold Spring Harbor Laboratory and Ausubel et al., 1999, *Current Protocols in Molecular Biology*, Greene Publishing and Wiley-Interscience, New York). For recent reviews on chemokines, see Ward et al., 1998, *Immunity* 9:1-11 and Baggiolini et al., 1998, *Nature* 392:565-568, and the references cited therein. Also see the CFB (*Cytokine Facts Book*, 1997, Academic Press Ltd.) and the GenBank databases. Additional references are provided infra.

The chemokines used in, or to prepare, the compositions of the present invention may be natural (i.e., have the sequence of a naturally occurring chemokine), may be the product of in vitro recombination of polynucleotides encoding naturally occurring chemokines, or may be synthetic (i.e., chemically synthesized) or recombinant variants of naturally occurring chemokine sequences. Chemokines comprise sequences from human, primate, rodent, viral, and other species. In some embodiments, xenogeneic sequences are used in the vaccination methods of the invention (e.g., if the most potent chemokine is from a species other than the species of the subject being immunized) because any immunogenic effects will likely enhance the adjuvant activity.

Exemplary Chemokine Compositions

In embodiments of the invention, the compositions contain at least one chemokine polypeptide that is an APC chemotaxin. In an embodiment, the chemokine is chemotactic for human immature (antigen uptake competent) monocyte derived dendritic cells.

To determine the chemotactic profile of a comprehensive set of known chemokines, in vitro chemotaxis assays were performed. A number of known chemokines are chemotactic for immature but not mature dendritic cells, including: hMIP1α, hMIP1α (70aa), mMIP-1α, hRANTES, hMET-RANTES, mRANTES, hHCC-1, hMPIF-1, hMPIF-1 (22-137), hMPIF-1 (46-137), hMIP-1δ, hMCP-4, mMCP-5, mMARC, mEotaxin, mMCP-1 (JE), mTECK, mMIP-2, mBLC, hLeukotactin, mMIG, and mMIP-1α. Other particularly useful chemokines of the invention include hMCP-2, hMCP-3, vMIP-1, hMIP-3α, hMIP-3β, and vMCK-2 (see Examples, infra). Several chemokines are chemotactic for immature dendritic cells but not chemotactic for neutrophils and other cell types tested in the in vitro assays (mC10, mMDC, hMIP-1β, mMIP-1γ; Table 3). These chemokines and their variants and derivatives are especially useful in the compositions and methods of the invention.

TABLE 3

Immature Dendritic Cell-Specific Chemotaxins

| | Immature DCs | Mature DCs | Monocytes | Neutrophils | Eosinophils | CEM (T-Cell line)[1] |
|---|---|---|---|---|---|---|
| mC10 | + | − | − | − | − | − |
| mMDC | + | − | − | − | − | − |
| hMIP-1β | + | − | − | − | − | − |
| mMIP-1γ | + | − | − | − | − | − |

[1]ATTC No. CCL-119.

Homologs and Variants of Naturally Occurring Chemokines

In one embodiment, an APC chemotaxin molecule has the sequence of a naturally occurring chemotaxin molecule, or has an amino acid sequence with substantial amino acid sequence identity to, the sequence of a naturally occurring chemotaxin molecule. For example, chemokine polypeptides, such as the chemokines listed supra, can be modified in ways that do not change the chemotactic properties of the naturally occurring polypeptide, for example, by conservative amino acid substitutions, truncations (especially at the termini), small internal deletions, insertions, and the like. Such modifications can be made using routine genetic engineering techniques, e.g., site-directed mutagenesis, and the resulting mutants assessed for chemotactic properties (e.g., using the assays disclosed herein).

In addition, recombinant and synthetic techniques can be used to modify naturally occurring chemokine molecules or sequences (including, but not limited to those listed supra and in Table 3) to modify the chemotactic properties of the polypeptide compared to the parent polypeptide(s).

Engineered Chemokines

In one aspect of the invention, synthetic, genetically engineered or recombinant chemotaxins are prepared and assessed for the ability to mobilize APCs (e.g., dendritic cells). In one embodiment, APC chemotaxins are generated from a combination of natural chemokines using synthetic or recombinant DNA technology. For example, different chemokines (e.g., human, viral, murine, and the like) can be recombined (e.g., genetically) to form chimeras or "hybrikines" that are tested for the desired activity (e.g., the ability attract immature dendritic cells but not neutrophils, enhanced chemoattractant activity at lower concentrations). In a related embodiment, the chimeras are chemically synthesized based on the sequence of parent (e.g., naturally occurring) chemokines.

In one embodiment, the sequences of chemokine polypeptides of interest are divided into four 'domains' as dictated by the spacing of the cysteine residues (see FIG. 2 and Examples). Alternatively, the sequences are divided into multiple "domains" (e.g. 2,3,4, or more) of any length (but typically at least 5, more often at least 10 residues), for the purpose of constructing hybrids. The sequences are conceptually recombined to form chimeric sequences in which one region has a sequence of a first chemokine polypeptide and a second region has the sequence of a second chemokine polypeptide, as illustrated in FIG. 2. Chimeric polypeptides (hybrikines) having the chimeric sequence are then produced by routine synthetic means (or alternatively, by using recombinant DNA techniques, as described infra), Polypeptide synthetic methods are well known in the art and are described in, e.g., U.S. Pat. No. 4,108,846; see also, Caruthers et al., 1980, *Nucleic Acids Res. Symp. Ser.*, 215-223; Horn et al., 1980, *Nucleic Acids Res. Symp. Ser.*, 225-232; Roberge, et al., 1995, *Science* 269:202). If desired, short polypeptides may be fused by condensation of the amino terminus of one molecule with the carboxyl terminus of the other molecule to form a peptide bond to produce a longer polypeptide. The newly synthesized peptide can be substantially purified, for example, by preparative high performance liquid chromatography (e.g., Creighton, 1983, *Proteins, Structures, and Molecular Principles*, W. H. Freeman and Co, New York N.Y.).

In an alternate embodiment, the polynucleotides encoding parent chemokines of interest are manipulated to produce variant or chimeric chemokines, such as those described supra (e.g., the polynucleotide is divided into multiple 'domains' as dictated by the spacing of the cysteine residues of the encoded polypeptide and hybrid gene constructs) or chemically synthesized polynucleotides are prepared. The hybrid genes are subcloned into appropriate expression vectors and introduced (e.g., transfected) into host cells (e.g., bacterial or eukaryotic cells) and the cells are cultured under conditions in which the recombinant protein is expressed. Supernatants of transfected cells are assayed for the desired chemoattractant properties using the assays described supra. Techniques for nucleic acid manipulation and expression are described generally, e.g., in Sambrook, et al., 1989, *Molecular Cloning: A Laboratory Manual* (2d ed.), vols. 1-3, Cold Spring Harbor Laboratory; and Ausubel, et al. (eds.) (supplemented to 1999) *Current Protocols in Molecular Biology*, Greene and Wiley, NY.

In an embodiment, a chimeric molecule comprises at least 10 contiguous residues from each of at least two different naturally occurring chemokines. In an embodiment, at least one of the naturally occurring chemokines, often two, and sometimes at least three or more of the chemokines, are selected from: hMIP 1α, hMIP1α (70aa), mMIP-1α, hRANTES, hMET-RANTES, mRANTES, hHCC-1, hMPIF-1, hMPIF-1 (22-137), hMPIF-1 (46-137), hMIP-1δ, hMCP-4, mMCP-5, mMARC, mEotaxin, mMCP-1 (JE), mTECK, mMIP-2, mBLC, hLeukotactin, mMIG, and mMIP-1β, hMCP-2, hMCP-3, vMIP-1, hMIP-3α, hMIP-3β, vMCK-2, and especially, mC10, mMDC, hMIP-1β, and mMIP-1γ. In an embodiment, the at least two different naturally occurring chemokines are from different species.

Derivatives of naturally occurring chemokines with enhanced dendritic cell attractant properties and decreased recruitment of non-dendritic immune cells, are constructed using different hybrids of human and viral chemokines. For example, an APC chemotaxin (e.g. a chemokine) with potent dendritic cell chemotactic activity but undesired neutrophil chemotactic activity can be recombined with a polypeptide with weaker dendritic cell activity and no neutrophil chemotactic activity to produce a polypeptide with strong dendritic cell activity, but lacking neutrophil chemotactic activity.

APC Chemotaxins Produced by Gene Shuffling Chemokine Polynucleotides

In one embodiment, derivatives of chemokines with enhanced properties (e.g. the ability attract immature dendritic cells but not neutrophils, enhanced chemoattractant activity at lower concentrations, and the like) are constructed using forced in vitro genetic evolution using any of several routine techniques, including error-prone PCR or recombination/gene shuffling approaches. Methods for generating new polypeptides with desired activities by gene "shuffling" are known in the art. Various shuffling methods are described in Patten et al., 1997, *Curr. Opin. Biotech.* 8:724-733; Stemmer, 1994, *Nature* 370:389-391; Stemmer et al., 1994, *Proc. Natl. Acad. Sci. USA* 91:10747-10751; Zhao et al., 1997, *Nucleic Acids Res.* 25:1307-1308; Crameri et al., 1998, *Nature* 391:288-291; Crameri et al., 1997, *Nat. Biotech.* 15:436-438; Arnold et al., 1997, *Proc. Natl. Acad. Sci. USA* 94:4504-4509; Crameri et al., 1996, *Nat. Biotechnol.* 14:315-319; Crameri et al., 1996, *Nat. Med.* 2:100-102; PCT publications WO95/22625; WO97/20078; WO97/35957; WO97/35966; WO98/13487; WO98/13485; PCT 98/00852; PCT 97/24239; and U.S. Pat. Nos. 5,605,793, 5,811,238, and 5,928,905. One method of gene shuffling involves conducting a polynucleotide amplification process on overlapping segments of a population of variants of a polynucleotide under conditions whereby one segment serves as a template for extension of another segment, to generate a population of recombinant polynucleotides, and screening or selecting a recombinant polynucleotide or an expression product thereof for a desired property. Some methods of shuffling use random point mutations (typically introduced in a PCR amplification step) as a source of diversity. The resulting polypeptides are tested for chemotactic activity as described above.

In an embodiment, gene shuffling is carried out beginning with a polynucleotide encoding a particular chemokine (e.g., hMCP2, hMCP3, hMIP1β, hMIP3α, hMIP3β, mMIG, mMIP1γ, mMDC, vMIP1, mC10). In a different embodiment, "family shuffling" is used (see, e.g., Cramer et al., 1998, *Nature* 152:88-91; Chang et al., 1999, *Nat Biotechnol* 17:793-7), and at least two "parental" chemokine-encoding polynucleotides are used in the family shuffling reaction. In an embodiment, at least one of the parental chemokine-encoding polynucleotides encodes hMIP1α, hMIP1α (70aa), mMIP-1α, hRANTES, hMET-RANTES, mRANTES, hHCC-1, hMPIF-1, hMPIF-1 (22-137), hMPIF-1 (46-137), hMIP-6δ, hMCP-4, mMCP-5, mMARC, mEotaxin, mMCP-1 (JE), mTECK, mMIP-2, mBLC, mMIP-1γ, mMIG, and mMIP-1β, hMCP-2, hMCP-3, vMIP-1, hMIP-3α, hMIP-3β, mC10, mMDC, hMIP-1β, vMCK-2, and hLeukotactin or a species homolog thereof.

In a related embodiment, at least two of the parental chemokine-encoding polynucleotides encode a chemokine from the group hMIP1α, hMIP1α (70aa), mMIP-1α, hRANTES, hMET-RANTES, mRANtes, hHCC-1, hMCP-3, vMIP-1, hMIP-3α, hMIP-3β, mC10, mMDC, hMIP-1hLeukotactin.

In an embodiment, the resulting shuffled ("evolved") molecule comprises at least 10 contiguous residues from at least one, often at least two different naturally occurring chemokines, e.g., such as the sets listed supra.

Other APC Chemotaxins Prepared by Mutating of Chemokine Molecules

In other aspects of the invention, a parental APC chemotaxin (e.g., chemokine) is modified by conventional in vitro mutagenesis methods (e.g., site directed mutagenesis (Ausubel, supra) or in vitro genetic manipulation of chemokine-encoding polynucleotides. The activity of the resulting variant can be determined using the in vitro and in vivo assays described herein.

In another aspect of the invention, a parental APC chemotaxin polypeptide (e.g., a chemokine) is modified (e.g., by in vitro genetic manipulation of the chemokine-encoding polynucleotide) to produce an amino- or carboxy-truncated version of the mature protein. Alternatively, these truncated version of the APC chemotaxin can be chemically synthesized or produced by enzymatic processing of a naturally occurring chemokine. In addition, variants with conservative substitutions that retain the desired properties may be used in the methods and compositions of the invention. Conservative substitution tables providing functionally similar amino acids are well known in the art. For example, one exemplary guideline to select conservative substitutions includes (original residue followed by exemplary substitution): ala/gly or ser; arg/lys; asn/gln or his; asp/glu; cys/ser; gln/asn; gly/asp; gly/ala or pro; his/asn or gln; ile/leu or val; leu/ile or val; lys/arg or gln or glu; met/leu or tyr or ile; phe/met or leu or tyr; ser/thr; thr/ser; trp/tyr; tyr/trp or phe; val/ile or leu.

An alternative exemplary guideline uses the following six groups, each containing amino acids that are conservative substitutions for one another:
(1) Alanine (A), Serine (S), Threonine (T)
(2) Aspartic acid (D), Glutamic acid (E)
(3) Asparagine (N), Glutamine (Q); 4) Arginine (R), Lysine (K)
(5) Isoleucine (I), Leucine (L), Methionine (M), Valine (V), and
(6) Phenylalanine (F), Tyrosine (Y), Tryptophan (W); (see also, e.g., Creighton (1984)*Proteins,* W. H. Freeman and Company; Schulz and Schimer (1979) *Principles of Protein Structure,* Springer-Verlag).

Polypeptide Mimetics

Polypeptide mimetics are also suitable for use in the methods of the invention. The terms "mimetic" and "peptidomimetic" refer to a synthetic chemical compound that has substantially the same structural and/or functional characteristics as an APC chemotaxin polypeptide of the invention (e.g., a specific chemokine). The mimetic can be either entirely composed of synthetic, non-natural analogues of amino acids or is a chimeric molecule of partly natural peptide amino acids and partly non-natural analogs of amino acids. The mimetic can also incorporate any amount of natural amino acid conservative substitutions as long as such substitutions do not substantially alter the mimetic's structure and/or activity. Polypeptide mimetic compositions can contain any combination of nonnatural structural components, which are typically from three structural groups: (a) residue linkage groups other than the natural amide bond ("peptide bond") linkages; (b) non-natural residues in place of naturally occurring amino acid residues; or (c) residues which induce secondary structural mimicry, i.e., inducing or stabilizing a secondary structure, e.g., a β turn, γ turn, β sheet, α helix conformation, and the like.

A polypeptide can be characterized as a mimetic when all or some of its residues are joined by chemical means other than natural peptide bonds. Individual peptidomimetic residues can be joined by peptide bonds, other chemical bonds or coupling means, such as, e.g., glutaraldehyde, N-hydroxysuccinimide esters, bifunctional maleimides, N,N'-dicyclohexylcarbodiimide (DCC) or N,N'-diisopropylcarbodiimide (DIC). Linking groups that can be an alternative to the traditional amide bond ("peptide bond") linkages include, e.g., ketomethylene (e.g., —C(=O)—CH$_2$— for —C(=O)—NH—), aminomethylene (CH$_2$—NH), ethylene, olefin (CH=CH), ether (CH$_2$—O), thioether (CH$_2$—S), tetrazole (CN$_4$—), thiazole, retroamide, thioamide, or ester (see, e.g., Spatola (1983) in *Chemistry and Biochemistry of Amino Acids, Peptides and Proteins*, Vol. 7, pp 267-357, "Peptide Backbone Modifications," Marcell Dekker, NY).

A polypeptide can also be characterized as a mimetic by containing all or some non-natural residues in place of naturally occurring amino acid residues. Nonnatural residues are well described in the scientific and patent literature; a few exemplary nonnatural compositions useful as mimetics of natural amino acid residues and guidelines are described below.

Mimetics of aromatic amino acids can be generated by replacing by, e.g., D- or L-naphylalanine; D- or L-phenylglycine; D- or L-2 thieneylalanine; D- or L-1, -2, 3- or 4-pyreneylalanine; D- or L-3 thieneylalanine; D- or L-(2-pyridinyl)-alanine; D- or L-(3-pyridinyl)-alanine; D- or L-(2-pyrazinyl)-alanine; D- or L-(4-isopropyl)-phenylglycine; D-(trifluoromethyl)-phenylglycine; D-(trifluoromethyl)-phenylalanine; D-p-fluorophenylalanine; D- or L-p-biphenylphenylalanine; K- or L-p-methoxybiphenylphenylalanine; D- or L-2-indole(alkyl) alanines; and, D- or L-alkylainines, where alkyl can be substituted or unsubstituted methyl, ethyl, propyl, hexyl, butyl, pentyl, isopropyl, iso-butyl, sec-isotyl, iso-pentyl, or a non-acidic amino acids. Aromatic rings of a nonnatural amino acid include, e.g., thiazolyl, thiophenyl, pyrazolyl, benzimidazolyl, naphthyl, furanyl, pyrrolyl, and pyridyl aromatic rings.

Mimetics of acidic amino acids can be generated by substitution by, e.g., non-carboxylate amino acids while maintaining a negative charge; (phosphono)alanine; sulfated threonine. Carboxyl side groups (e.g., aspartyl or glutamyl) can also be selectively modified by reaction with carbodiimides (R'—N—C—N—R') such as, e.g., 1-cyclohexyl-3 (2-morpholinyl-(4-ethyl) carbodiimide or 1-ethyl-3(4-azonia-4,4-dimetholpentyl) carbodiimide. Aspartyl or glutamyl can also be converted to asparaginyl and glutaminyl residues by reaction with ammonium ions.

Mimetics of basic amino acids can be generated by substitution with, e.g., (in addition to lysine and arginine) the amino acids ornithine, citrulline, or (guanidino)-acetic acid, or (guanidino)alkyl-acetic acid, where alkyl is defined above. Nitrile derivative (e.g., containing the CN-moiety in place of COOH) can be substituted for asparagine or glutamine. Asparaginyl and glutaminyl residues can be deaminated to the corresponding aspartyl or glutamyl residues.

Arginine residue mimetics can be generated by reacting arginyl with, e.g., one or more conventional reagents, including, e.g., phenylglyoxal, 2,3-butanedione, 1,2-cyclohexanedione, or ninhydrin, preferably under alkaline conditions.

Tyrosine residue mimetics can be generated by reacting tyrosyl with, e.g., aromatic diazonium compounds or tetranitromethane. N-acetylimidizol and tetranitromethane can be used to form O-acetyl tyrosyl species and 3-nitro derivatives, respectively.

Cysteine residue mimetics can be generated by reacting cysteinyl residues with, e.g., α-haloacetates such as 2-chloroacetic acid or chloroacetamide and corresponding amines; to give carboxymethyl or carboxyamidomethyl derivatives. Cysteine residue mimetics can also be generated by reacting cysteinyl residues with, e.g., bromo-trifluoroacetone, α-bromo-β-(5-imidozoyl) propionic acid; chloroacetyl phosphate, N-alkylmaleimides, 3-nitro-2-pyridyl disulfide; methyl 2-pyridyl disulfide; p-chloromercuribenzoate; 2-chloromercuri-4 nitrophenol; or, chloro-7-nitrobenzo-oxa-1,3-diazole.

Lysine mimetics can be generated (and amino terminal residues can be altered) by reacting lysinyl with, e.g., succinic or other carboxylic acid anhydrides. Lysine and other α-amino-containing residue mimetics can also be generated by reaction with imidoesters, such as methyl picolinimidate, pyridoxal phosphate, pyridoxal, chloroborohydride, trinitrobenzenesulfonic acid, O-methylisourea, 2,4, pentanedione, and transamidase-catalyzed reactions with glyoxylate.

Mimetics of methionine can be generated by reaction with, e.g., methionine sulfoxide. Mimetics of proline include, e.g., pipecolic acid, thiazolidine carboxylic acid, 3- or 4-hydroxy proline, dehydroproline, 3- or 4-methylproline, or 3,3,-dimethylproline. Histidine residue mimetics can be generated by reacting histidyl with, e.g., diethylprocarbonate or para-bromophenacyl bromide.

Other mimetics include, e.g., those generated by hydroxylation of proline and lysine; phosphorylation of the hydroxyl groups of seryl or threonyl residues; methylation of the α-amino groups of lysine, arginine and histidine; acetylation of the N-terminal amine; methylation of main chain amide residues or substitution with N-methyl amino acids; or amidation of C-terminal carboxyl groups. A component of a natural polypeptide can also be replaced by an amino acid (or peptidomimetic residue) of the opposite chirality. Thus, any amino acid naturally occurring in the L-configuration (also referred to as the R or S, depending upon the structure of the chemical entity) can be replaced with the amino acid of the same chemical structural type or a peptidomimetic, but of the opposite chirality, generally referred to as the D-amino acid, but which can additionally be referred to as the R— or S— form.

The mimetics of the invention can also include compositions that contain a structural mimetic residue, particularly a residue that induces or mimics secondary structures, such as a β turn, γ sheet, a helix structures, ≡ turns, and the like. For example, substitution of natural amino acid residues with D-amino acids; N-α-methyl amino acids; C-α-methyl amino acids; or dehydroamino acids within a peptide can induce or stabilize β turns, γ turns, β sheets or α helix conformations. 3 turn mimetic structures have been described, e.g., by Nagai (1985) *Tet. Lett.* 26:647-650; Feigl (1986) *J. Amer. Chem. Soc.* 108:181-182; Kahn (1988) *J. Amer. Chem. Soc.* 110:1638-1639; Kemp (1988) *Tet. Lett.* 29:5057-5060; Kahn (1988)*J. Molec. Recognition* 1:75-79. β sheet mimetic structures have been described, e.g., by Smith (1992) *J. Amer. Chem. Soc.* 114:10672-10674. For example, a type VI β turn induced by a cis amide surrogate, 1,5-disubstituted tetrazol, is described by Beusen (1995) *Biopolymers* 36:181-200. Incorporation of achiral omega-amino acid residues to generate polymethylene units as a substitution for amide bonds is described by Banerjee (1996) *Biopolymers* 39:769-777. Secondary structures of polypeptides can be analyzed by, e.g., high-field 1H NMR or 2D NMR spectroscopy; see, e.g., Higgins (1997) *J. Pept. Res.* 50:421435. See also, Hruby (1997) *Biopolymers*43:219-266, Balaji, et al, U.S. Pat. No. 5,612,895.

Specific examples of mimetics which can be incorporated into the polypeptides of the invention include those described by, e.g, Zhang (1998) Biochemistry 37:12465-12476, who constructed functionally active (R and S)-γ-lactam conformational mimetics using a 3-(R or S)-amino-2-oxo-1-pyrrolidine-acetamido moiety in place of the Pro-Gly of the tridecapeptide *Saccharomyces cerevisiae* α-factor mating pheromone. Brady (1998) *J. Med. Chem.* 41:401-406, used a resin-based route for the synthesis of thrombin inhibitor mimetic with a range of lipophilic carboxylic amides. Baures (1997, *J. Med. Chem.* 40:3594-3600) constructed a diketopiperazine conformational mimic into a L-prolyl-L-leucylglycinamide structure and into the bicyclic lactam PLG peptidomimetic structure of dopamine receptor. Beaulieu (1997, *J. Med. Chem.* 40:2164-2176) used a (hydroxyethyl)amidosuccinoyl core to synthesize a peptidomimetic structure to inhibit HIV viral protease activity. Misicka (1997, *J. Pept. Res.* 50:48-54) designed mimetics of deltorphin I and dermenkephalin containing stereoisomer of the unusual amino acid beta-methylphenylalanine to generate peptides with increased ligand binding specificity.

The skilled artisan will recognize that individual synthetic residues and polypeptides incorporating mimetics can be synthesized using a variety of procedures and methodologies that are well described in the scientific and patent literature, e.g., *Organic Syntheses Collective Volumes,* Gilman et al. (Eds) John Wiley & Sons, Inc., NY. Polypeptides incorporating mimetics can also be made using solid phase synthetic procedures as described, e.g., by Di Marchi, et al., and U.S. Pat. No. 5,422,426. Mimetics of the invention can also be synthesized using combinatorial methodologies. Various techniques for generation of peptide and peptidomimetic libraries are well known, and include, e.g., multipin, tea bag, and split-couple-mix techniques; see, e.g., al-Obeidi (1998) *Mol. Biotechnol.* 9:205-223; Hruby (1997) *Curr. Opin. Chem. Biol.* 1:114-119; Ostergaard (1997) *Mol. Divers.* 3:17-27; and Ostresh (1996) *Methods Enzymol.* 267:220-234.

Small Chemokine Mimetics

In an embodiment, small molecule chemokine mimetics are used to mobilize APCs. Typically, small molecule mimetics are identified using high throughput screening technologies for small molecule compounds that bind chemokine receptors (CRs) and transduce signal (e.g., calcium ion mobilization or other chemokine receptor-mediated responses). For example, small molecules can be screened initially for the ability to agonize chemokine receptors that are expressed on immature dendritic cells and/or are not expressed on other cells (see, e.g., Table 2B). The agonizing activity can be detected in a variety of ways, such as detecting Ca2+ mobilization responses on transfectant cells expressing cloned chemokine receptors known to be present on APCs.

The chemotactic properties of the molecules are then determined using the assays described supra, and those with desired specificity (e.g., chemotactic for immature but not mature dendritic cells) are used in the methods of the present invention.

Chemotactic Compositions

The chemotactic compositions of the invention contain one or more APC chemotaxins or chemotaxin-encoding polynucleotides. In an embodiment, the composition contains an APC chemotaxin that is an isolated or recombinant polynucleotide or polypeptide. In an embodiment, the APC chemotaxin(s) is/are the predominant species (i.e., greater than about 50%, more often greater than about 80% by weight of the total of the members of the class of molecule in the composition) of its class (e.g., polypeptide, polynucleotide, lipid, carbohydrate) in the composition. In other embodiments, the APC chemotaxin(s) is "biologically pure." The words "isolated," "pure" "substantially purified" or "biologically pure" refer to material that is substantially or essentially free from components which normally accompany it as found in its native state. Thus, in an embodiment, the chemotactic compositions of the invention contain APC chemotaxins free of materials normally associated with their in situ environment (if naturally occurring). Typically, the isolated, chemotaxins of the invention are at least about 80% pure, usually at least about 90%, and preferably at least about 95%. Protein purity or homogeneity may be determined by a number of means well known in the art, such as polyacrylamide gel electrophoresis of a protein sample, followed by visualization upon staining. For certain purposes high resolution will be needed and HPLC or a similar means for purification utilized.

In embodiments, the compositions may additionally contain an excipient or carrier, such as described infra. In some embodiments of the invention, the composition includes one or more antigens (i.e., the antigen to which it is desired to induce or enhance an immune response), as is discussed in greater detail infra.

In embodiments, the compositions may contain a conventional adjuvant. Conventional adjuvants typically convert soluble protein antigens into particulate material and often include bacteria or bacterial products. Exemplary conventional adjuvants include Freund's incomplete adjuvant, Freund's complete adjuvant, Merck Adjuvant 65, AS-2, alum, aluminum phosphate, mineral gels such as aluminum hydroxide, and surface active substances such as lysolecithin, pluronic polyols, polyanions, peptides, oil emulsions, keyhole limpet hemocyanin, and dinitrophenol. Other useful adjuvants include, but are not limited to, bacterial capsular polysaccharides, dextran, 1L-12, GM-CSF, CD40 ligand, IFN-γ, IL-1, IL-2, IL-3, IL-4, IL-10, IL-13, IL-18 or any cytokine.

In one aspect, the invention provides a method of formulating a composition capable of inducing an immune response (that is, the composition possesses the characteristic of being able to elicit an immune response if administered) to a specified antigen in a subject by identifying a polypeptide having the activity of an antigen-presenting cell chemotaxin (APC chemotaxin) as described herein and combining the polypeptide with the antigen. In an embodiment, a pharmaceutically acceptable excipient is also included.

Antigens

In one aspect, the present invention provides a method of eliciting or enhancing an immune response to an antigen, e.g., a predetermined or specified antigen. An antigen is a molecule that reacts with an antibody. In some embodiments the antigen is an immunogen. In some embodiments the antigen is linked to a protein carrier. For example, in one embodiment of the invention, an APC chemotaxin and an antigen are physically linked (e.g., made as a fusion protein, stably cross-linked using chemical cross-linkers, or linked via complexes such as biotin and streptavidin).

An antigen is typically a peptide, a polypeptide, chemical compound, microbial pathogen, bacteria (e.g., live, attenuated, or inactivated), a virus (including inactivated virus particles, modified live viral particles, and recombinant virus particles), a recombinant cell, glycoproteins, lipoproteins, glycopeptides, lipopeptides, toxoids, carbohydrates, tumor-specific antigens, and other immunogenic components of pathogens. In one embodiment, mixtures of two or more antigens are employed. In some embodiments, the antigen is biologically pure.

In one embodiment, the methods and reagents of the invention are used to provide protection from exogenous foreign infectious pathogenic agents (such as bacteria, virus, and the like) prior to expected or possible exposure. In a related embodiment, the methods and reagents of the invention are used to provide therapeutic effects against exogenous foreign pathogens to which an individual has been exposed or to an individual displaying symptoms of exposure.

In one embodiment, reagents and methods of the invention are used to treat cancers, including, but not limited to, melanomas, lung cancers, thyroid carcinomas, breast cancers, renal cell carcinomas, squamous cell carcinomas, brain tumors and skin cancers. In one embodiment, the antigen is a tumor-associated antigen (tumor specific-antigen). Tumor antigens are molecules, especially cell surface proteins, which are differentially expressed in tumor cells relative to non-tumor tissues (e.g., telomerase).

For prophylactic use, compositions containing APC chemotaxins are administered (e.g., in conjunction with antigens) to a subject susceptible to or otherwise at risk of a disease, e.g., a tumor, cancer, infection, and the like. For therapeutic use, compositions containing the APC chemotaxins are administered (e.g., in conjunction with antigens) to a subject once a disease, e.g. a tumor, cancer, infection, and the like, is detected or diagnosed, or after surgical removal, e.g., of tumors.

Exemplary antigens or vaccine components of the invention include antigens derived from microbial pathogens such as bacteria [e.g., Pertussis (*Bordetella pertussis*, inactivated whole organism); Cholera (*Vibrio cholerae*, whole killed organism); Meningitis (*Neisseria meningitidis*, polysaccharide from organism); Lyme Disease (*Borrelia burgdorferi*, lipoprotein OspA); Haemophilus B (*Haemophilus influenza* B polysaccharide, Tetanus conjugate or OmpC); Pneumonia (*Streptococcs pneumoniae* capsular polysaccharide) Typhoid (*Salmonella typhi* polysaccharide vaccine, killed whole organism)], viruses including inactivated virus particles, modified live viral particles, and recombinant virus particles to Influenza virus; Hepatitis A; Hepatitis B; Measles; Rubella virus; Mumps; Rabies; Poliovirus; Japanese Encephalitis virus; Rotavirus; Varicella], Diphtheria (*Corynebacterium diphtheriae*) and Tetanus (*Clostridium tetani*).

Polynucleotide Chemotactic Compositions

In one aspect, the APC chemotaxin, the antigen, or both are delivered as DNA such that the polypeptides are generated in situ. In one embodiment, the DNA is "naked," as described, for example, in Ulmer et al., Science 259:1745-1749, 1993 and reviewed by Cohen, 1993, Science 259: 1691-1692. The uptake of naked DNA may be increased by coating the DNA onto a carrier, e.g. biodegradable beads, which is efficiently transported into the cells. In such vaccines, the DNA may be present within any of a variety of delivery systems known to those of ordinary skill in the art, including nucleic acid expression systems, bacterial and viral expression systems. Techniques for incorporating DNA into such expression systems are well known to those of ordinary skill in the art. See, e.g., WO90/11092, WO93/24640, WO 93/17706, and U.S. Pat. No. 5,736,524.

Vectors, used to shuttle genetic material from organism to organism, can be divided into two general classes: Cloning vectors are replicating plasmid or phage with regions that are non-essential for propagation in an appropriate host cell and into which foreign DNA can be inserted; the foreign DNA is replicated and propagated as if it were a component of the vector. An expression vector (such as a plasmid, yeast, or animal virus genome) is used to introduce foreign genetic material into a host cell or tissue in order to transcribe and translate the foreign DNA, such as APC chemotaxin. In expression vectors, the introduced DNA is operably-linked to elements such as promoters that signal to the host cell to transcribe the inserted DNA. Some promoters are exceptionally useful, such as inducible promoters that control gene transcription in response to specific factors. Operably-linking an APC chemotaxin and/or antigen polynucleotide to an inducible promoter can control the expression of an APC chemotaxin and/or antigen polypeptide or fragments. Examples of classic inducible promoters include those that are responsive to α-interferon, heat shock, heavy metal ions, and steroids such as glucocorticoids (Kaufman, 1990. Methods Enzymol 185:487-511.) and tetracycline. Other desirable inducible promoters include those that are not endogenous to the cells in which the construct is being introduced, but, however, are responsive in those cells when the induction agent is exogenously supplied. In general, useful expression vectors are often plasmids. However, other forms of expression vectors, such as viral vectors (e.g., replication defective retroviruses, adenoviruses and adeno-associated viruses) are contemplated.

Vector choice is dictated by the organism or cells being used and the desired fate of the vector. Vectors may replicate once in the target cells, or may be "suicide" vectors. In general, vectors comprise signal sequences, origins of replication, marker genes, enhancer elements, promoters, and transcription termination sequences.

Administration of APC Chemotaxin and Antigen

In embodiments, the compositions can contain one or more antigens (or antigen-encoding polynucleotides). The antigens can be administered in combination with the APC chemotaxin (i.e., in the same mixture). Alternatively, they can be administered separately.

In one aspect, the invention provides an immunization method in which a combination of one or more antigens (or antigen-encoding polynucleotides) and one or more APC chemotaxins (or an APC chemotaxin-encoding polynucleotides) are administered to a subject. Optionally, the antigen or APC chemotaxin is administered in a delivery vehicle such as a physiologically acceptable excipient.

Administration and Dose Scheduling

In one embodiment of the invention, an antigen is administered simultaneously with the chemotactic composition. In an alternative embodiment, the antigen and the chemotactic composition are administered at different times, typically to the same site. For example, the chemotactic composition (without the antigen) can be administered between about 15 minutes and about 96 hours prior to the administration of the antigen, more often between about 15 minutes and about 48 hours, more often between 24 hours and 96 hours, often between about 48 hours and 72 hours or between 72 hours and 96 hours prior to the administration of the antigen.

When the chemotactic composition and an antigen composition are injected at the same site in a subject, preferably the injections are within 2 cm of each other, preferably within 1 cm or preferably within 0.5 cm of each other on the two dimensional surface of the body. In this embodiment, the administrations should also be done to a similar depth and to the same tissue layer (i.e., both injections should be subcutaneous or both intradermal). For intramuscular injections, the depth should be more precisely monitored to achieve a three dimensional equivalent placement of the APC chemotaxin and the antigen to within 2 cm of each other, preferably to within 1 cm, and more preferably to within 0.5 cm. This is easily accomplished by physicians, nurses and other medically trained personal. The injection site can be marked with an indelible ink to assist the physician.

In one embodiment, only one dose (administration) of the composition is given. In another embodiment, the first administration is followed by boosting doses. In an embodiment, the APC chemotaxin is administered in multiple doses, often in combination with an antigen (e.g., by co-administration). In various embodiments, the APC chemotaxin composition (optionally including antigen) is administered once, twice, three times, or more than three times. The number of doses administered to a subject is dependent upon the antigen, the extent of the disease, and the response of a subject to the chemotactic composition. It will be appreciated that it is within the scope of the present invention that a suitable number of doses includes any number required to immunize an animal (i.e., to a predetermined antigen).

In one embodiment of the invention, a second administration (booster) of the chemotactic composition and antigen occurs between about 7 days and 1 year after the original administration. In an embodiment, a second administration (booster) of the chemotactic composition and antigen occurs between about 14 days and 6 months after the original administration. Alternatively, a second administration (booster) of the chemotactic composition and antigen occurs between about 21 days and 3 months after the original administration, often between about 28 days and 2 months after the original administration. In one embodiment third administration (second booster) occurs between about 14 days and 10 years after the original administration, e.g., between about 14 days and 3 years after the original administration, often between about 21 days and 1 year after the original administration, very often between about 28 days and 6 months after the original administration. Subsequent boosters may be administered at 2 week intervals, or 1 month, 3 month or 6 month to 10 year intervals.

It will be recognized by those of ordinary skill that a variety of vaccine administration doses and schedules can be developed based upon the parameters discussed above and known in the art, and that determination of an effective amount and number of doses of chemotaxins of the invention, antigens, or some combination of chemotaxin(s) and antigen(s) for administration is well within the capabilities of those skilled in the art.

Effective Dose

Typically, the amount of APC chemotaxin and antigen will be administered to a subject that is sufficient to immunize an animal against an antigen (i.e., an "immunologically effective dose" or a "therapeutically effective dose"). An amount adequate to accomplish an "immunologically effective dose" will depend on, e.g., the APC chemotaxin and antigen composition, the manner of administration, the stage and severity of the disease being treated, the weight and general state of health of the subject, and the judgment of the prescribing physician.

The effective dose of antigen and APC chemotaxin can be formulated in animal models to achieve an induction of an immune response using techniques that 2° are well known in the art. One having ordinary skill in the art can readily optimize administration to humans based on animal data. When the APC chemotaxin is a polypeptide, such as a chemokine, a dose will typically be between about 1 fg and about 100 µg, often between about 1 pg and about 100 µg, more often between about 1 ng and about 50 µg, and usually between about 100 ng and about 50 µg. In some embodiments, the dose is between about 1 fg and about 100 µg per kg subject body weight, often between about 1 pg and about 100 µg, more often between about 1 ng and about 50 µg, and usually between about 100 ng and about 50 µg per kg subject body weight.

The amount of antigen that is administered will vary with the identity and characteristics of the antigen. In one embodiment, a chemotactic composition of the present invention contains one or more antigens and one or more chemotaxins at a molar or weight ratio of about 1:1000 or greater, chemotaxin to antigen. In another embodiment, the ratio of chemotaxin to antigen in the composition is between about 1:10 and 1:1000. In another embodiment, the ratio of antigen to chemotaxin in the composition is between about 1:10 and 1:1000, or greater than 1:1000 or greater. In another embodiment, the ratio of antigen to chemotaxin in the composition is between about 1:10 and 10:1.

Carriers, Excipients, Conventional Adjuvants, Mode of Administration

The APC chemotaxin-containing compositions of the invention may be administered in a variety of ways, as described herein. In various embodiments, the chemotactic composition includes carriers and excipients (including but not limited to buffers, carbohydrates, mannitol, proteins, polypeptides or amino acids such as glycine, antioxidants, bacteriostats, chelating agents, suspending agents, thickening agents and/or preservatives), water, oils, saline solutions, aqueous dextrose and glycerol solutions, other pharmaceutically acceptable auxiliary substances as required to approximate physiological conditions, such as buffering agents, tonicity adjusting agents, wetting agents and the like, and/or a conventional adjuvant (e.g., as discussed supra). It will be recognized that, while any suitable carrier known to those of ordinary skill in the art may be employed to administer the compositions of this invention, the type of carrier will vary depending on the mode of administration. Compounds may also be encapsulated within liposomes using well-known technology. Biodegradable microspheres may also be employed as carriers for the pharmaceutical compositions of this invention. Suitable biodegradable microspheres are disclosed, for example, in U.S. Pat. Nos. 4,897,268; 5,075,109; 5,928,647; 5,811,128; 5,820,883; 5,853,763; 5,814,344 and 5,942,252.

The compositions of the invention may be sterilized by conventional, well-known sterilization techniques, or may be sterile filtered. The resulting aqueous solutions may be packaged for use as is, or lyophilized, the lyophilized preparation being combined with a sterile solution prior to administration.

The APC chemotaxin composition of the invention may be administered in a variety of ways, including by injection (e.g., intradermal, subcutaneous, intramuscular, intraperitoneal and the like), by inhalation, by topical administration, by suppository, by using a transdermal patch or by mouth.

When administration is by injection, the chemotaxin(s) may be formulated in aqueous solutions, preferably in physiologically compatible buffers such as Hanks solution, Ringer's solution, or physiological saline buffer. The solution may contain formulatory agents such as suspending, stabilizing and/or dispersing agents. Alternatively, the chemotactic composition may be in powder form for constitution with a suitable vehicle, e.g., sterile pyrogen-free water, before use.

When administration is by inhalation, the chemotaxin(s) may be delivered in the form of an aerosol spray from pressurized packs or a nebulizer with the use of a suitable propellant, e.g., dichlorodifluoromethane, trichlorofluoromethane, carbon dioxide or other suitable gas. In the case of a pressurized aerosol, the dosage unit may be determined by providing a valve to deliver a metered amount. Capsules and cartridges of, e.g., gelatin for use in an inhaler or insufflator may be formulated containing a powder mix of the proteins and a suitable powder base such as lactose or starch.

When administration is by topical administration, the chemotactic composition may be formulated as solutions, gels, ointments, creams, suspensions, and the like, as are well known in the art. In some embodiments, administration is by means of a transdermal patch.

When administration is by suppository (e.g., rectal or vaginal), compositions may also be formulated in compositions containing conventional suppository bases.

When administration is oral, a composition can be readily formulated by combining the chemotaxin with pharmaceutically acceptable carriers well known in the art. A solid carrier, such as mannitol, lactose, magnesium stearate, and the like may be employed; such carriers enable the chemotaxin to be formulated as tablets, pills, dragees, capsules, liquids, gels, syrups, slurries, suspensions and the like, for oral ingestion by a subject to be treated. For oral solid formulations such as, for example, powders, capsules and tablets, suitable excipients include fillers such as sugars, cellulose preparation, granulating agents, and binding agents.

Nucleic acid molecules, such as those encoding APC chemotaxins, can be inserted into vectors and used as gene therapy vectors. Gene therapy vectors can be delivered to a subject by, for example, intravenous injection, local administration (Nabel et al., U.S. Pat. No. 5,328,470 1994. USA), or by stereotactic injection (Chen et al., 1994. Proc Natl Acad Sci USA 91:3054-7.). The pharmaceutical preparation of a gene therapy vector can include an acceptable diluent or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells that produce the gene delivery system.

Other convenient carriers, as well-known in the art, also include multivalent carriers, such as bacterial capsular polysaccharide, a dextran or a genetically engineered vector. In addition, sustained-release formulations the include, for example, APC chemotaxin molecules and/or antigens, allow for the release of APC chemotaxin over extended periods of time, such that without the sustained release formulation, the APC chemotaxin would be cleared from a subject's system, and/or degraded by, for example, proteases and simple hydrolysis before eliciting or enhancing an immune response.

Vaccination for Monoclonal and Polyclonal Antibody Production

Methods of producing polyclonal and monoclonal antibodies, including binding fragments (e.g., $F_{(ab)2}$) and single chain versions, are well known to those of skill in the art. See, e.g., Coligan, 1991, *Current Protocols in Immunology*, Wiley/Greene, NY; and Harlow and Lane, 1989, *Antibodies: A Laboratory Manual*, Cold Spring Harbor Press, NY. However, many antigens are not capable of triggering an adequate antibody response in animals. In one embodiment, a composition comprising a chemotaxin of the invention and an antigen is administered to an animal as described herein, thus inducing or enhancing the immune response in the animal. Polyclonal or monoclonal antibodies are subsequently prepared by standard techniques.

Stimulation of Innate Immune Response

In another aspect of the invention, the compositions of the invention are administered to a subject to stimulate the innate immune response. The innate immune response is body's initial defense against pathogens and is elicited by a variety of cells including APCs. These cells express surface and cytoplasmic receptors that recognize molecules of foreign origin (e.g., bacterial and viral nucleic acids, proteins, carbohydrates). Upon detecting these signals, the dendritic cells and macrophage elicit a defensive response that includes the release of cytokines (including interferons, TNF-α, and IL-12) and chemokines that attract cells such as immature dendritic cells, macrophage, NK cells, and granulocytes, to the site of challenge.

The compositions of the invention are useful, not only to attract dendritic cells and other cells to the site of administration, but also to stimulate these cells into eliciting elements of the innate immune response to confer non-specific protection while the body is generating the adaptive response.

In one embodiment, a composition of the invention is administered (without antigen) prior or post exposure of an anticipated infection. In another embodiment, the chemokine is administered with "foreign" molecules (e.g., bacterial or viral nucleic acids, proteins, carbohydrates, or synthetic elements which mimic these elements).

Kits

In an aspect, the invention provides kits containing one or more of the following in a package or container: (1) a chemotactic composition of the invention; (2) a pharmaceutically acceptable adjuvant or excipient; (3) an antigen (e.g., a biologically pure antigen); (4) a vehicle for administration, such as a syringe; (5) instructions for administration. Embodiments in which two or more of components (1)-(5) are found in the same container are also contemplated.

When a kit is supplied, the different components of the composition may be packaged in separate containers and admixed immediately before use. Such packaging of the components separately may permit long-term storage without losing the active components' functions.

(a) Containers, Packages and Vessels

The reagents included in the kits can be supplied in containers of any sort such that the life of the different components are preserved and are not adsorbed or altered by the materials of the container. For example, sealed glass ampules may contain lyophilized APC chemotaxin polypeptide or polynucleotide, or buffers that have been packaged under a neutral, non-reacting gas, such as nitrogen. Ampules may consist of any suitable material, such as glass, organic polymers, such as polycarbonate, polystyrene, etc.; ceramic, metal or any other material typically employed to hold similar reagents. Other examples of suitable containers include simple bottles that may be fabricated from similar substances as ampules, and envelopes, that may comprise foil-lined interiors, such as aluminum or an alloy. Other containers include test tubes, vials, flasks, bottles, syringes, or the like. Containers may have a sterile access port, such as a bottle having a stopper that can be pierced by a hypodermic injection needle. Other containers may have two compartments that are separated by a readily removable membrane that upon removal permits the components to be mixed. Removable membranes may be glass, plastic, rubber, etc. (b) Instructional Materials Kits may also be supplied with instructional materials. Instructions may be printed on paper or other substrate, and/or may be supplied as an electronic-readable medium, such as a floppy disc, CD-ROM, DVD-ROM, Zip disc, videotape, audiotape, etc. Detailed instructions may not be physically associated with the kit; instead, a user may be directed to an internet web site specified by the manufacturer or distributor of the kit, or supplied as electronic mail.

SELECTED CHEMOKINE REFERENCES mMIP-1α

Davatelis G, Tekamp-Olson P, Wolpe S D, Hermsen K, Luedke C, Gallegos C, Coit D, Merryweather J, Cerami A. Cloning and characterization of a cDNA for murine macrophage inflammatory protein (MIP), a novel monokine with inflammatory and chemokinetic properties. *J Exp Med.* Jun. 1, 1988;167(6):1939-44 hMET-RANTES

Proudfoot A E, Power C A, Hoogewerf A J, Montjovent M O, Borlat F, Offord R E, Wells T N. Extension of recombinant human RANTES by the retention of the initiating methionine produces a potent antagonist. *J Biol Chem.* Feb. 2, 1996;271(5): 2599-603.

mRANTES

Schall T J, Simpson N J, Mak J Y Molecular cloning and expression of the murine RANTES cytokine: structural and functional conservation between mouse and man. *Eur J Immunol.* June 1992;22(6):1477-81 mMCP-5

Sarafi M N, Garcia-Zepeda E A, MacLean J A, Charo I F, Luster A D. Murine monocyte chemoattractant protein (MCP)-5: a novel CC chemokine that is a structural and functional homologue of human MCP-1. *J Exp Med.* Jan. 6, 1997;185(1):99-109.

mMARC

Thirion S, Nys G, Fiten P, Masure S, Van Damme J, Opdenakker G. Mouse macrophage derived monocyte chemotactic protein-3: cDNA cloning and identification as MARC/FIC. *Biochem Biophys Res Commun.* Jun 15, 1994; 201(2):493-9 mEotaxin

Rothenberg M E, Luster A D, Leder P. Murine eotaxin: an eosinophil chemoattractant inducible in endothelial cells and in interleukin 4-induced tumor suppression. *Proc Natl Acad Sci USA.* Sep. 12, 1995;92(19):8960-4.

mMCP1 (JE)

Van Damme J, Decock B, Bertini R, Conings R, Lenaerts J P, Put W, Opdenakker G, Mantovani A. Production and identification of natural monocyte chemotactic protein from virally infected murine fibroblasts. Relationship with the product of the mouse competence (JE) gene. *Eur J Biochem.* Jul. 1, 1991;199(1):223-9.

MTECK

Vicari A P, Figueroa D J, Hedrick J A, Foster J S, Singh K P, Menon S, Copeland N G, Gilbert D J, Jenkins N A, Bacon K B, Zlotnik A. TECK: a novel CC chemokine specifically expressed by thymic dendritic cells and potentially involved in T cell development. *Immunity.* August 1997;7(2):291-301 mMIP-2

Tekamp-Olson P, Gallegos C, Bauer D, McClain J, Sherry B, Fabre M, van Deventer S, Cerami A. Cloning and characterization of cDNAs for murine macrophage inflammatory protein 2 and its human homologues. *J Exp Med.* Sep. 1, 1990;172(3):911-9.

mBLC

Gunn M D, Ngo V N, Ansel K M, Ekland E H, Cyster J G, Williams L T. A B-cell-homing chemokine made in lymphoid follicles activates Burkitt's lymphoma receptor-1. *Nature.* Feb. 19, 1998;391(6669):799-803.

mMIP-1γ

Poltorak A N, Bazzoni F, Smirnova II, Alejos E, Thompson P, Luheshi G, Rothwell N, Beutler B J MIP-1 gamma: molecular cloning, expression, and biological activities of a novel CC chemokine that is constitutively secreted in vivo. *Inflamm* 1995; 45(3):207-19 mMIG

Farber J M, A macrophage mRNA selectively induced by gamma-interferon encodes a member of the platelet factor 4 family of cytokines, *Proc Natl Acad Sci USA* July 1990;87 (14):5238-42.

mMIP1-β

Sherry B, Tekamp-Olson P, Gallegos C, Bauer D, Davatelis G, Wolpe S D, Masiarz F, Coit D, Cerami A. Resolution of the two components of macrophage inflammatory protein 1, and cloning and characterization of one of those components, macrophage inflammatory protein 1 beta. *J Exp Med.* Dec. 1, 1988;168(6):2251-9.

vMIP-1

Nicholas J, Ruvolo V R, Burns W H, Sandford G, Wan X, Ciufo D, Hendrickson S B, Guo H G, Hayward G S, Reitz M S. Kaposi's sarcoma-associated human herpesvirus-8 encodes homologues of macrophage inflammatory protein-1 and interleukin-6. *Nat Med.* March 1997;3(3):287-92 mC10

Orlofsky, A, Berger, M. S., and Prystowsky, M. B. Novel expression pattern of a new member of the MIP-1 family of cytokine-like genes. *Cell Regulation,* Vol 2, p403-412, 1991.

mMDC

Schaniel, C, E. Pardali, F. Sallusto, M. Speletas, C. Ruedl, T. Shimizu, T. Seidl, J. Andersson, F. Melchers, A. G. Rolink, and P. Sideras. Activated Murine B Lymphocytes and Dendritic Cells Produce a Novel CC Chemokine which Acts Selectively on Activated T Cells *J. Exp. Med.,* Volume 188, Number 3, Aug. 3, 1998 451-463 hLeukotactin

Youn B S, Zhang S M, Lee E K, Park D H, Broxmeyer H E, Murphy P M, Locati M, Pease J E, Kim K K, Antol K, Kwon B S. Molecular cloning of leukotactin-1: a novel human beta-chemokine, a chemoattractant for neutrophils, monocytes, and lymphocytes, and a potent agonist at CC chemokine receptors 1 and 3. *J Immunol.* Dec. 1, 1997;159 (11):5201-5 hMIP-1β

Lipes, M. A. et al., (1988) Identification, cloning, and characterization of an immune activation gene. *Proc. Natl. Acad. Sci. U.S.A* 85:9704.

hMCP-2

Van Damme J, Proost P, Lenaerts J P, Opdenakker G. Structural and functional identification of two human, tumor-derived monocyte chemotactic proteins (MCP-2 and MCP-3) belonging to the chemokine family. *J Exp Med.* Jul. 1, 1992;176(1):59-65.

hMCP-3

Van Damme J, Proost P, Lenaerts J P, Opdenakker G. Structural and functional identification of two human, tumor-derived monocyte chemotactic proteins (MCP-2 and MCP-3) belonging to the chemokine family. *J Exp Med.* Jul. 1, 1992;176(1):59-65.

hMIP-3α

Hieshima K, Imai T, Opdenakker G, Van Damme J, Kusuda J, Tei H, Sakaki Y, Takatsuki K, Miura R, Yoshie O, Nomiyama H. Molecular cloning of a novel human CC chemokine liver and activation-regulated chemokine (LARC) expressed in liver. Chemotactic activity for lymphocytes and gene localization on chromosome 2. *J. Biol. Chem.* Feb. 28, 1997;272(9):5846-53.

hMIP-3β

Yoshida R, Imai T, Hieshima K, Kusuda J, Baba M, Kitaura M, Nishimura M, Kakizaki M, Nomiyama H, Yoshie 0. Molecular cloning of a novel human CC chemokine EBI1-ligand chemokine that is a specific functional ligand for EBI1, CCR7. *J Biol Chem.* May 23, 1997;272(21):13803-9 hRANTES

Schall, T. et al., (1988) A human T cell-specific molecule is a member of a new gene family. *J. Immunol.* 141:1018.

hMIP1α

Obaru K, Fukuda M, Maeda S, Shimada K. A cDNA clone used to study mRNA inducible in human tonsillar lymphocytes by a tumor promoter. *J Biochem (Tokyo).* March 1986;99(3):885-94.

hMIP1α (70aa)

Irving et al., 1990, Two inflammatory mediator cytokine genes are closely linked and variably amplified on chromosome 17q. *Nuc. Acid Res.* 18:3261-70 hHCC-1

Schulz-Knappe P, Magert H J, Dewald B, Meyer M, Cetin Y, Kubbies M, Tomeczkowski J, Kirchhoff K, Raida M, Adermann K, et al. HCC-1, a novel chemokine from human plasma. *J Exp Med.* Jan. 1, 1996;183(1):295-9.

hMPIF-1

Forssmann U, Delgado M B, Uguccioni M, Loetscher P, Garotta G, Baggiolini M. CK beta8, a novel CC chemokine that predominantly acts on monocytes. *FEBS Lett.* May 19, 1997;408(2):211-6 hMPIF-1 (22-137)

Youn B S, Zhang S M, Broxmeyer H E, Cooper S, Antol K, Fraser M Jr, Kwon B S. Characterization of CK beta8 and CK beta8-1: two alternatively spliced forms of human beta-chemokine, chemoattractants for neutrophils, monocytes, and lymphocytes, and potent agonists at CC chemokine receptor 1. *Blood.* May 1, 1998;91(9):3118-26.

hMPIF-1 (46-137)

Macphee C H, Appelbaum E R, Johanson K, Moores K E, Imburgia C S, Fomwald J, Berkhout T, Brawner M, Groot P H, O'Donnell K O'Shannessy D, Scott G, White J R. Identification of a truncated form of the CC chemokine CK beta-8 demonstrating greatly enhanced biological activity. *J Immunol.* Dec. 1, 1998;161(11):6273-9.

hMIP-1δ

Wang, W. et al., (1998) Molecular cloning and functional characterization of human MIP-1 delta, a new C—C chemokine related to mouse CCF-18 and C10. *J. Clin. Immunol.* 18(3):214.

hMCP-4

Uguccioni, M. et al., (1996) Monocyte chemotactic protein 4 (MCP4), a novel structural and functional analogue of MCP-3 and eotaxin. *J. Exp. Med.* 183:2379.

m6Ckine

Hedrick J A, Zlotnik A. Identification and characterization of a novel beta chemokine containing six conserved cysteines. *J Immunol.* Aug. 15, 1997;159(4):1589-93.

hSDF1α

Tashiro K, Tada H, Heilker R, Shirozu M, Nakano T, Honjo T Signal sequence trap: a cloning strategy for secreted proteins and type I membrane proteins. *Science.* Jul. 30, 1993;261(5121):600-3.

Nagasawa T, Kikutani H, Kishimoto T. Molecular cloning and structure of a pre-B-cell growth-stimulating factor. *Proc Natl Acad Sci USA.* Mar. 15, 1994;91 (6):2305-9.

hSDF1β

Tashiro K, Tada H, Heilker R, Shirozu M, Nakano T, Honjo TSignal sequence trap: a cloning strategy for secreted proteins and type I membrane proteins. *Science.* Jul. 30, 1993;261(5121):600-3.

mSDF1α

Bleul C C, Fuhlbrigge R C, Casasnovas J M, Aiuti A, Springer T A. A highly efficacious lymphocyte chemoattractant, stromal cell-derived factor 1 (SDF-1). *J Exp Med.* Sep. 1, 1996;184(3):1101-9.

vMCK-2

Saederup N, Lin Y C, Dairaghi D J, Schall T J, Mocarski E S. Cytomegalovirus-encoded beta chemokine promotes monocyte-associated viremia in the host. *Proc Natl Acad Sci USA.* Sep. 14, 1999;96(19):10881-6.

MacDonald M R, Burney M W, Resnick S B, Virgin H W. Spliced mRNA encoding the murine cytomegalovirus chemokine homolog predicts a beta chemokine of novel structure. *J. Virol.* May 1999;73(5):3682-91.

See also GenBank, e.g., accession no. AF124602 (vMCK-2), accession no. P10147 (hMIP1α), accession no. P10855 (mMIP-1α), accession no. P13501 (hRANTES), accession no. P30882 (mRANTES), accession no. Q16627 (hHCC-1), accession no. P55773 (hMPIF-1), accession no. Q16663 (hMIP-1δ), accession no. Q99616 (hMCP-4), accession no. Q62401 (mMCP-5), accession no. Q03366 (mMARC), accession no. P48298 (mEotaxin), accession no. P10148 (mMCP-1 (JE)), accession no. O35903 (mTECK), accession no. P10889 (mMIP-2), accession no. AF044196 (mBLC), accession no. P18340 (mMIG), accession no. P14097 (mMIP-1β), accession no. P80075 (hMCP-2), accession no. P80098 (hMCP-3), accession no. P78556 (hMIP-3α), accession no. Q99731 (hMIP-3β), accession no. P27784 (mC10), accession no. AJ238238 (mMDC), accession no. P13236 (hMIP-1β), and accession no. P51670 (mMIP-1γ).

EXAMPLES

Example 1

Chemotaxis assays were carried out using purified cells and a 96-well chemotaxis microchamber (ChemoTx®, NeuroProbes, Inc., Gaithersburg, Md.). In this assay, a porous polycarbonate filter was used to allow formation of a chemoattractant concentration gradient across the filter, as well as to allow cells to migrate into the filter or through into the lower well.

To perform an immature dendritic cell chemotaxis assay, 29 μl of a candidate or known APC chemotaxin at 0, 1, 10 and 100 nM CHECK concentrations were placed in the wells of the lower chamber. The filter was placed on the top of the chamber, so that the chemoattractant solution touched the under side of the filter. Day 7 immature dendritic cells were harvested, washed once with chemotaxis buffer containing 0.1% BSA (Sigma) in HBSS ((Life Technologies), with $Ca^{++}$ and $Mg^{++}$), and finally resuspended in chemotaxis buffer at $5\times10^6$ per ml. Twenty microliters of cells were carefully placed onto the filter. Migration was allowed to proceed for 90 minutes at 37° C. in a tissue culture incubator. Migration was terminated by removing non-migrating cells on the top of the filter using a rubber scrapper. The filter was removed from the apparatus and rinsed with DPBS. (The lower chamber was inspected microscopically to determine if any cells had migrated into the wells. If a significant number of cells were present in the wells, quantification was done in the wells as well as the filter). To detect those cells that had migrated into the polycarbonate filter in the immature dendritic cell migration assay, the filter, after being removed from the apparatus and rinsed with DPBS (Hyclone), was stained with a cell staining solution such as the Hema3 staining kit (Fisher Scientific). The filter was immersed into the three separate solutions sequentially, each for approximately 5 seconds. After the last solution, the filter was rinsed in water several times. The filter was allowed to air dry and the signal was determined by reading the filter on a plate reader (Molecular Devices) at wavelength 540 nm. The magnitude of migration was calculated as the ratio of absorbance between the wells with chemoattractants and the wells with chemotaxis buffer alone.

Example 2

Chemokine Injection Into Mice

This example describes an in vivo assay in which the ability of several chemokines to attract dendritic cells is demonstrated.

The following chemokines were obtained from R&D Systems (Minneapolis, Minn.): MCP2, MCP3, MIP1β, MIP3α, MIP3β, RANTES, mMIG, mMDC, mC10, vMIP1. Each chemokine (2 μg in PBS) was injected intradermally into a different BALB/c mouse. One mouse received a control injection of PBS with no chemokine. Seventy-two hours after injection, the mice were euthanized, and the area around the injection site was excised and subjected to immunohistology. Frozen sections were stained with anti-DEC-205 antibody (available from Bio-Whittaker Molecular Applications, Rockland, Me.; Kraal et al., 1986, *J. Exp. Med.* 163:981), which recognizes a surface molecule specific to dendritic cells. A relative staining number on a scale of 0 to 5 was assigned to each section (0=lowest infiltration, 5 highest infiltration). Results are shown in Table 4.

Several chemokines elicited a DEC-205+(dendritic cell) infiltration to the site of injection after 72 hours when injected intradermally. Of these MCP3, MIP3β, mMIG, mMDC, mC10, and viral MIP1 showed DC infiltration; MCP3, mMDC and mC10 showed the best infiltration.

TABLE 4

Dendritic Cell Infiltration in vivo Assay

| Chemokine | DC Infiltration |
| --- | --- |
| MCP2 | 0 |
| MCP3 | 3 |
| MIP1b | 0 |
| MIP3a | 0 |
| MIP3β | 1 |
| RANTES | 0 |
| mMIG | 2 |

TABLE 4-continued

Dendritic Cell Infiltration in vivo Assay

| Chemokine | DC Infiltration |
| --- | --- |
| mMDC | 3 |
| mC10 | 4 |
| vMIP1 | 0 |
| PBS | 0 |

Example 3

Chemokine Injection Into Rhesus monkeys, Experiment 1

This example demonstrates that certain chemokines injected intradermally to a non-human primate elicit mononuclear infiltration to the site of injection.

Coded, sterile chemokines (2 μg in PBS) were injected intradermally (100 μl injection volume) into the upper arm of Rhesus macaques under anesthesia. In each case, two monkeys were each given two injections of the same chemokine at two different locations (e.g. left arm versus right arm). After 72 hours, one injection site was punch-biopsied and separated into an edge and a center sample and both samples were prepared for immunohistology. After 96 hours, the other injection site was punch-biopsied and separated into an edge and a center sample, and both samples were prepared for immunohistology. The results are presented in Table 5, wherein each row represents a single animal. A section of the prepared tissue was stained with hematoxalin and eosin, and mononuclear cells were identified by morphology (e.g., being mononuclear in contrast to polynuclear). GM-CSF (200 μg doses) and RANTES (20 μg doses) were used as positive controls. Injection of PBS and analysis of non-injected tissues were used as negative controls.

Mononuclear cell infiltration was score based on the following scale of 0 to 5: 0=a very mild perivascular mononuclear inflammatory infiltrate seen throughout the dermis; 1=a mild perivascular mononuclear inflammatory infiltrate seen throughout the dermis; 2=a mild/moderate perivascular mononuclear inflammatory infiltrate seen throughout the dermis; 3=a moderate perivascular mononuclear inflammatory infiltrate seen throughout the dermis; 4=an extensive perivascular mononuclear inflammatory infiltrate seen throughout the dermis; 5=a florid perivascular mononuclear inflammatory infiltrate seen throughout the dermis. Intermediate scores are indicated, e.g., "2/3" represents a score between 2 and 3. GM-CSF (200 μg dose) showed between a 2 and 3 level of infiltration at 72 hours, as did RANTES (20 μg). Additional internally coded samples of RANTES (20 μg dose) showed up to a 2 level of infiltration. Negative controls (PBS) usually had a 0 level of infiltrate Of the chemokines tested, MCP-2, MCP-3, MIP-1, MIP3α, MIP3β, RANTES, mMIG, mMDC, mC10, and viral MIP1 showed mononuclear infiltration, with mMDC, mC10, and viral MIP1 showing the highest level of infiltration. In general, greater infiltration was apparent after 72 hours than after 96 hours.

TABLE 5

Mononuclear Cell Infiltration

| | 72 h | | 96 h | |
|---|---|---|---|---|
| Chemokine | Center | Edge | Center | Edge |
| GM-CSF (200 ug)* | 0 | 0 | 3 | 2/3 |
| RANTES (20 ug)* | 0/1 | 1 | 2/3 | 1/2 |
| MCP2 | 1/2 | 1 | 1/2 | 1 |
| MCP2 | 1 | 0/1 | 0 | 0 |
| MCP3 | 1/2 | 0 | Not Determined | 0 |
| MCP3 | 0/1 | 0/1 | 0/1 | 1 |
| MIP1b | 0 | 0/1focal | 1 | 0 |
| MIP1b | 1/2focal | 0/1 | 0 | 0 |
| MIP3a | 1 | 1/2 | 0/1 | 0/1 |
| MIP3a | 2 | 1/2focal | 1/2 | 0/1 |
| MIP3β | 2 | 1 | 0 | 1/2 |
| MIP3β | 1/2 | 1/2focal | 2 | 1/2focal |
| RANTES | 0 | 2 | 0 | 1/2focal |
| RANTES | 1/2 | 0/1 | 1/2focal | 0/1 |
| mMIG | 0/1 | 1 | 0/1 | 0/1 |
| mMIG | 0 | 0/2focal | 0 | 0/1 |
| mMDC | 1/2 | 1/2 | 0 | 1 |
| mMDC | 0/1 | 2/3focal | 2 | 2/3focal |
| mC10 | 3/4 | 1/2 | 1/2focal | 1 |
| mC10 | 3/4 | 1/2 | 1/2 | 1/2focal |
| vMIP1 | 2 | 0/1 | 0/1 | 1 |
| vMIP1 | 2 | 1/2 | 2/3 | 2/3 |

Key:
"*" used as positive controls. Each horizontal row represents a separate Rhesus macaque and the histology scores of the 4 samples assayed form each animal. "Focal" one vessel in the section showed prominent perivascular inflammation (i.e., one section of the slide around a vessel showed prominent infiltration, where as the rest of the slide was more or less normal). "Center" and "Edge" refer to where the tissue section came from. "Center" tissue sections were taken at the site of intradermal injection; "Edge" tissue sections were taken further from the injection site, towards the edge of the wheal generated by injection Example 4

Chemokine Injection into Rhesus monkeys Experiment 2

In a second experiment, different amounts (approximately 8, 2.4, or 0.8 μg in 100 μl PBS) of different chemokines were injected intradermally in Rhesus macaques under anesthesia. Twenty-four or 48 hours later, 6 mm skin punch biopsies were taken using aseptic technique, then bisected and prepared for analysis. One portion of the biopsy was embedded in OCT compound, flash frozen and stored at −70° C. The other portion of the biopsy was fixed in formalin and embedded in paraffin wax; subsequently, sections were stained with hematoxylin and eosin and microscopically examined for cell infiltration into the dermis (Table 6). As a negative control, monkeys were injected with PBS lacking chemokines.

Mononuclear cell infiltration in the dermis was scored as in Example 3. As indicated in Table 6, chemokines mC10 and vMCK-2 caused substantial mononuclear cell infiltration, especially at 24 hours. It was notable that a chemokine encoded by a mouse virus (vMCK-2) exhibited potent activity in primate cells. Infiltrating cells were observed predominantly in adipose tissue, although cells were also noted in the subcutaneous region and, in the case of vMCK-2 at 48 hours, in the collagen matrix of the superficial dermis. Chemokines mMDC and vMIP-1 caused less inflammation than mC10 and vMCK-2.

TABLE 6

Mononuclear Cell Infiltration

| Chemokine | 24 hr | 48 hr |
|---|---|---|
| mC10: | | |
| 0.8 μg | 2 | 0 |
| 2.4 μg | 1 | 2 |
| 8 μg | 3 | 2 |
| mMDC: | | |
| 0.8 μg | 2 | 0 |
| 2.4 μg | 0 | 0 |
| 8 μg | 2 | 0 |
| vMIP-1: | | |
| 0.8 μg | 0 | 0 |
| 2.4 μg | 1 | 0 |
| 8 μg | 0 | 0 |
| vMCK-2: | | |
| 0.8 μg | 2 | 2 |
| 2.4 μg | 2 | 2 |
| 8 μg | 4 | 3 |

Example 5

Chemokine Injection in Rhesus Macques, Experiment 3

In a third experiment, greater amounts of vMCK-2, mC10 and vMIP-1 (60, 20, or 8 μg) were injected intradermally in Rhesus macaques under anesthesia. As before, biopsies were taken 24 and 48 hours later, then prepared and analyzed histologically (Table 7). Samples were scored as in Example 3. As shown before in Example 4, vMCK-2 was observed to cause a dramatic infiltration of mononuclear cells as well as polynuclear cells; the 20 μg injection caused more infiltration than did the 60 μg and 8 μg injections. vMIP-1 caused a mild infiltration at all doses tested. In contrast to the previous two experiments (Examples 4 and 5) where lower chemokine concentrations were used, mC10 caused little to no infiltration in this experiment.

TABLE 7

Mononuclear Cell Infiltration

| | | 24 hours | | 48 hours | |
|---|---|---|---|---|---|
| Chemokine | Dose | monkey 1 | monkey 2 | monkey 3 | monkey 4 |
| vMIP-1 | 60 μg | 1 | | 1 | |
| | 20 μg | | 1 | | 0 |
| | 8 μg | 0 | | 0 | |
| C10 | 60 μg | 0 | | 0 | |
| | 20 μg | | 0 | | 0 |
| | 8 μg | | 1 | | 0 |
| vMCK-2 | 60 μg | 3 | | 3 | |
| | 20 μg | | 4 | | 2 |
| | 8 μg | | 3 | | 1 |
| saline | | 0 | 1 | 0 | 0 |

To better define the identity of the infiltrating cells, samples from the last two monkey studies (i.e. Tables 6 and 7) were analyzed by immunohistochemistry using antibodies specific for different cell types. These antibodies included CD68 (expressed on macrophages, neutrophils and dendritic cells), MHC II (antigen-presenting cells, e.g. macrophages and dendritic cells), HAM-56 (macrophages), fascin (dendritic cells, endothelial cells and epithelial cells), elastase (neutrophils), cytokeratin (epithelial cells), CD3 (T cells), CD20 (13 cells), and CD1a (angerhans cells). The vMCK-2-injected skin samples contained primarily neutrophils and antigen-presenting cells, including macrophages and dendritic cells. The mC10-injected skin samples contained primarily antigen-presenting cells, including macrophages and dendritic cells, but few neutrophils. The vMIP-1-injected skin samples contained primarily neutrophils and macrophages, with few dendritic cells. Few T cells, and no B cells, were found in the skin samples for each of the three chemokines.

Example 6

Chemokine Adjuvant Activity In Rhesus Monkeys

Since the chemokines mC10 and vMCK-2 recruited antigen-presenting cells, including dendritic cells, to the site of injection, these two chemokines were tested for their ability to act as an immunization adjuvant to augmenting the immune response to a co-injected foreign antigen. Five groups of monkeys, 3 monkeys per group, were injected intradermally with chicken ovalbumin (OVA) as an antigen. The first group of monkeys received OVA alone while the second group contained OVA emulsified 1:1 with incomplete Freund's adjuvant (IFA), a standard adjuvant that is typically required in such studies to enable development of an antigen-specific immune response. The third group contained OVA plus IFA plus vMCK-2, while the fourth group contained OVA plus IFA plus mC10. The fifth group contained OVA plus vMCK-2, without IFA. Injections were done intradermally in a 100 µl volume containing 2 mg OVA and 16 µg chemokine. Ten ml of peripheral blood was drawn from each monkey twice a week for three weeks and the blood samples were then subjected to centrifugation over Ficoll to remove the erythrocytes and granulocytes. The plasma supernatant was analyzed by sandwich ELISA to determine the levels of anti-OVA antibodies using OVA-coated plastic dishes and a biotinylated anti-monkey IgG detection antibody (Table 8).

TABLE 8

Induction of anti-OVA Antibodies

|  | day 0 | day 5 | day 9 | day 12 | day 16 | day 19 |
| --- | --- | --- | --- | --- | --- | --- |
| OVA | 266 | 240 | 222 | 396 | 376 | 597 |
|  | 817 | 549 | 880 | 757 | 907 | 1262 |
|  | 87 | 62 | 106 | 69 | 87 | 85 |
| OVA + IFA | 35 | 28 | 103 | 5515 | 10877 | 10621 |
|  | 71 | 78 | 58 | 6436 | 20324 | 25011 |
|  | 93 | 58 | 89 | 4175 | 12340 | 20596 |
| OVA + IFA + vMCK2 | 133 | 92 | 129 | 1194 | 1738 | 2737 |
|  | 114 | 88 | 157 | 5581 | 52320 | 16276 |
|  | 181 | 140 | 104 | 9215 | 10437 | 46055 |
| OVA + IFA + mC10 | 95 | 89 | 125 | 19537 | 51204 | 32014 |
|  | 107 | 86 | 129 | 29317 | 38857 | 32282 |
|  | 144 | 133 | 129 | 12057 | 31480 | 34211 |
| OVA + vMCK2 | 25 | 44 | 38 | 140 | 413 | 462 |
|  | 77 | 89 | 76 | 330 | 313 | 275 |
|  | 89 | 30 | 28 | 128 | 279 | 368 |

Key:
Numbers represent the levels of OVA-specific IgG, expressed in Units/ml, in the plasma of the 15 monkeys. Each horizontal line shows the response of an individual monkey over time after immunization. To determine the levels of OVA-specific IgG, dilutions of each plasma sample were analyzed by sandwich ELISA using OVA-coated plates together with a biotinylated anti-monkey IgG detection antibody. Optical densities were converted into arbitrary Units, where a Unit is defined as the inverse of the plasma dilution that produces 50% of the maximum response from a standard curve obtained by serial dilution of an ascites collected from OVA injected mice and containing OVA-specific antibodies.

As indicated in table 8, the monkeys injected with OVA+IFA developed a significant antibody response to OVA, as demonstrated by development of circulating anti-OVA IgG, commencing day 12. In comparison, the levels of OVA-specific IgG in the monkeys injected with OVA, mC10 and IFA were substantially greater than those in monkeys not receiving mC10. Specifically, the inclusion of mC10 lead to approximately four-fold more OVA-specific IgG on day 12, and three-fold more OVA-specific IgG on both days 16 and 19 compared to monkeys injected with just OVA+IFA alone.

While less potent than mC10, vMCK-2 also exhibited the capacity to augment the OVA-specific antibody response. Two of the three monkeys injected with OVA+IFA+vMCK-2 exhibited significantly more circulating OVA-specific IgG than those of the monkeys injected with OVA+IFA alone, as observed on day 16 for one monkey and day 19 for the other. The third monkey failed to develop an OVA-specific IgG response that was significantly different from monkeys receiving OVA alone, most likely due to a technical error in immunization of this monkey. Monkeys receiving OVA plus vMCK-2 alone, i.e., in the absence of IFA, failed to elicit a significant antigen-specific OVA response.

Example 7

(Prophetic)

This example describes a procedure to evaluate the efficacy of APC chemotaxins in augmenting systemic and/or mucosal immune responses to infectious diseases.

Groups of mice are injected either subcutaneously, intradermally, intranasally, or by any other mode with varying doses of the virus, bacterium or parasite under study, using a typical immunization schedule, e.g., days 0, 7, and 14, in the presence or absence of APC chemotaxin given simultaneously with the microorganism in an appropriate formulation. Serum and/or mucosal secretions are collected on days-7, 0, 7, 14, 21, 28 and 35 for antigen-specific antibody analysis by ELISA. Mice are sacrificed at different time intervals after the last immunization to quantitate the antigen-specific antibody-forming cells and antigen-specific T cell responses (both cytotoxic and helper T cell populations) present in immune compartments, using standard procedures.

Example 8

(Prophetic)

This example describes a procedure to evaluate the efficacy of APC chemotaxins to augment anti-tumor immunity in cancer immunotherapy regimens.

While many tumor cells express unique tumor-associated antigens, these antigens are invariably weak immunogens and fail to generate potent anti-tumor immunity during tumor progression. The ability of APC chemotaxins to augment protective anti-tumor immunity can be evaluated using a model system of cancer immunotherapy in mice. In this model, mice are transplanted with a syngeneic thymoma (EL4 cells) that have previously been transfected with the experimental protein antigen OVA. Without further intervention, the tumor grows and eventually kills the mouse. Animals can be at least partially protected by vaccinating them with OVA plus adjuvant to induce an antigen-specific immune response directed against the OVA-transfected thymoma cells. This model is an effective way to evaluate the relative efficacy of adjuvants in augmenting protective anti-tumor immunity. Positive controls in this model include the following adjuvants: CFA, IFA, alum and GM-CSF. The ability of APC chemotaxins to augment cancer immunotherapy regimens can be evaluated by comparison to these known adjuvants.

Example 9

(Prophetic)

Design of Hybrikines

"Hybrikines" are chimeric chemokine polypeptides designed to generate novel molecules with the appropriate, desired, and enhanced qualities. Usually, the amino acid sequence of a desired hybrikines is determined, and the molecule is produced by chemical synthesis.

The sequences of chemokines hMCP-2, mC10 and mMDC are conceptually divided into functional domains based on the spacing of the invariant cysteine residues. Chimeric sequences are prepared by swapping domains between these molecules. The amino termini regions (all amino acids of the mature native protein amino terminal of the first conserved cysteine residue) are swapped onto the remaining portion of a different chemokine molecule to create hybrids. As shown in FIG. 2, the amino terminal regions between mC10 and hMCP-2 create two novel molecules: the mC10/hMCP2 and hMCP2/mC10 "hybridkine" molecules. In addition, the amino terminal regions between mMDC and hMCP-2 are swapped to create an additional two novel molecules: the mMDC/hMCP2 and hMCP2/mMDC "hybrikine" molecules. These polypeptides are synthesized chemically using classical Fmoc peptide chemistry. The chemotactic abilities of these polypeptides are then tested in in vitro and in vivo chemotaxis assays.

The present invention provides novel methods and materials relating to APC-chemotactic compositions and therapeutic and prophylactic immunization. While specific examples have been provided, the above description is illustrative and not restrictive. Many variations of the invention will become apparent to those of skill in the art upon review of this specification. The scope of the invention should, therefore, be determined not with reference to the above description, but instead should be determined with reference to the appended claims along with their full scope of equivalents.

All publications and patent documents cited in this application are incorporated by reference in their entirety for all purposes to the same extent as if each individual publication or patent document were so individually denoted.

The invention claimed is:

1. A pharmaceutical composition comprising viral murine cytomegalovirus chemokine 2 (vMCK-2) and an antigen.

2. The pharmaceutical composition of claim 1, further comprising a pharmaceutically acceptable excipient.

3. The pharmaceutical composition of claim 1, further comprising an adjuvant.

4. The pharmaceutical composition of claim 1, further comprising an additional chemokine.

5. The pharmaceutical composition of claim 1, wherein the chemokine and antigen are linked.

6. The pharmaceutical composition of claim 1, wherein the antigen is a tumor-associated antigen.

7. The pharmaceutical composition of claim 1, wherein the antigen is derived from a microbial pathogen.

8. The pharmaceutical composition of claim 7, wherein the microbial pathogen is a bacterium.

9. The pharmaceutical composition of claim 7, wherein the microbial pathogen is a virus.

10. The pharmaceutical composition of claim 1, wherein the composition is encapsulated in a liposome.

11. The phannaceutical composition of claim 1, wherein the composition is encapsulated in a microsphere.

12. The pharmaceutical composition of claim 1 which is sterile.

13. The pharmaceutical composition of claim 12, wherein the composition is suitable for peritoneal administration.

14. The pharmaceutical composition of claim 12, wherein the composition is formulated for administration by injection.

15. The pharmaceutical composition of claim 12, wherein the composition is formulated for administration by inhalation.

16. The pharmaceutical composition of claim 12, wherein the composition is formulated for topical application.

17. The pharmaceutical composition of claim 12, wherein the composition is formulated for oral administration.

18. The pharmaceutical composition of claim 12, wherein the composition is formulated for administration by suppository.

19. A pharmaceutical composition comprising mC10 and an antigen.

20. The pharmaceutical composition of claim 19, further comprising a pharmaceutically acceptable excipient.

21. The pharmaceutical composition of claim 19, further comprising an adjuvant.

22. The pharmaceutical composition of claim 19, further comprising an additional chemokine.

23. The pharmaceutical composition of claim 19, wherein the chemokine and antigen are linked.

24. The pharmaceutical composition of claim 19, wherein the antigen is a tumor-associated antigen.

25. The pharmaceutical composition of claim 19, wherein the antigen is derived from a microbial pathogen.

26. The pharmaceutical composition of claim 25, wherein the microbial pathogen is a bacterium.

27. The pharmaceutical composition of claim 25, wherein the microbial pathogen is a virus.

28. The pharmaceutical composition of claim 19, wherein the composition is encapsulated in a liposome.

29. The pharmaceutical composition of claim 19, wherein the composition is encapsulated in a microsphere.

30. The pharmaceutical composition of claim 19 which is sterile.

31. The pharmaceutical composition of claim 30, wherein the composition is suitable for peritoneal administration.

32. The pharmaceutical composition of claim 30, wherein the composition is fonnulated for administration by injection.

33. The pharmaceutical composition of claim 30, wherein the composition is formulated for administration by inhalation.

34. The pharmaceutical composition of claim 30, wherein the composition is formulated for topical application.

35. The pharmaceutical composition of claim 30, wherein the composition is formulated for oral administration.

36. The pharmaceutical composition of claim 30, wherein the composition is formlated for administration by suppository.

* * * * *